US012778600B2

(12) United States Patent
El-Khatib

(10) Patent No.: US 12,778,600 B2
(45) Date of Patent: Nov. 3, 2026

(54) HAND-HELD MEDICAL INSTRUMENT

(71) Applicant: Walid El-Khatib, Berlin (DE)

(72) Inventor: Walid El-Khatib, Berlin (DE)

(*) Notice: Subject to any disclaimer, the term of this patent is extended or adjusted under 35 U.S.C. 154(b) by 128 days.

(21) Appl. No.: 18/692,952

(22) PCT Filed: Sep. 16, 2022

(86) PCT No.: PCT/EP2022/075839
§ 371 (c)(1),
(2) Date: Mar. 18, 2024

(87) PCT Pub. No.: WO2023/041741
PCT Pub. Date: Mar. 23, 2023

(65) Prior Publication Data

US 2024/0423646 A1 Dec. 26, 2024

(30) Foreign Application Priority Data

Sep. 19, 2021 (DE) ..................... 20 2021 003 055.7
Jan. 10, 2022 (DE) ..................... 20 2022 100 107.3
Jan. 26, 2022 (DE) ..................... 20 2022 100 457.9

(51) Int. Cl.
*A61B 17/16* (2006.01)
*A61B 17/00* (2006.01)

(52) U.S. Cl.
CPC *A61B 17/1659* (2013.01); *A61B 2017/00424* (2013.01); *A61B 2017/00438* (2013.01)

(58) Field of Classification Search
CPC .......... A61B 17/1659; A61B 5/150259; A61B 17/1635; A61B 2560/0418; A61B 2560/0425; B25G 1/102; B26B 21/522
See application file for complete search history.

(56) References Cited

U.S. PATENT DOCUMENTS

2004/0068265 A1* 4/2004 Parmigiani ........ A61B 17/1659
606/89
2007/0055264 A1* 3/2007 Parmigiani ........ A61B 17/1635
606/84

(Continued)

FOREIGN PATENT DOCUMENTS

DE 8531992 U1 1/1986
EP 1405602 A1 4/2004

(Continued)

OTHER PUBLICATIONS

Written Opinion and International Search Report, Application No. PCT/EP2022/075839, mailed Jan. 18, 2023, 16 pages.

(Continued)

*Primary Examiner* — Andrew Yang
(74) *Attorney, Agent, or Firm* — Francis J. Maguire; WARE FRESSOLA MAGUIRE & BARBER LLP

(57) ABSTRACT

A hand instrument is provided with a handpiece and a scraping blade arranged distally of the handpiece and a chip chamber (30), of which the scraping blade is designed for scraping in particular bones and is arranged in such a way that chips scraped by means of the scraping blade enter the chip chamber and the scraping blade extends in a plane inclined with respect to a longitudinal axis of the handpiece. The handpiece is designed as a handle with three finger rests and a proximal support rest, wherein the three finger rests are inclined to one another in such a way that the three finger rests extend in pairs at an angle of less than 90° to one another in a cross-section through the handpiece.

18 Claims, 30 Drawing Sheets

(56) References Cited

U.S. PATENT DOCUMENTS

| | | | | |
|---|---|---|---|---|
| 2007/0208348 | A1* | 9/2007 | Parmigiani | A61B 17/1659 606/84 |
| 2010/0005630 | A1 | 1/2010 | Gitman et al. | |
| 2015/0157469 | A1* | 6/2015 | Prado | A61F 2/4455 606/86 A |

FOREIGN PATENT DOCUMENTS

| | | | |
|---|---|---|---|
| EP | 1829486 | A1 | 9/2007 |
| EP | 2196162 | B1 | 10/2016 |
| WO | 9711646 | A1 | 4/1997 |
| WO | 2022149060 | A1 | 7/2022 |

OTHER PUBLICATIONS

Search Report, German Application No. 20 2022 100 107.3, dated Sep. 12, 2022, 5 pages.

ZEPF Catalog, p. 201, "Bone Scraper", zepf-dental.com, 2019 (1 page).

* cited by examiner d)

c)

b)

a)

HAND-HELD MEDICAL INSTRUMENT

CROSS REFERENCE TO RELATED APPLICATIONS

This application is the U.S. National Stage of International Application Number PCT/EP2022/075839 filed on Sep. 16, 2022, which claims priority to DE Application 20 2021 003 055.7 filed Sep. 19, 2021, DE Application 20 2022 100 107.3 filed Jan. 10, 2022, and DE Application 20 2022 100 457.9 filed Jan. 26, 2022, which applications are is hereby incorporated by reference in their entirety.

TECHNICAL FIELD

The invention relates to a medical hand instrument, in particular a disposable bone scraper, with a handpiece and a scraping blade and chip chamber arranged distally of the handpiece.

BACKGROUND OF THE INVENTION

Such hand instruments are used, for example, as bone scrapers in dentistry to obtain bone material for autologous bone grafting. For example, the transplantation of autologous bone is used to create a stable bone structure for dental implants.

The scraping blade of the hand instrument is in particular designed for scraping bones and is arranged in such a way that chips scraped by the scraping blade reach the chip chamber and are collected there for further use. In known hand instruments, the scraping blade extends in a plane inclined relative to a longitudinal axis of the handpiece.

The use of such a hand instrument requires great endurance and precision in handling from the user, e.g. a dentist or oral surgeon.

The inventor recognized that known medical hand instruments are deficient in this respect and do not facilitate the user's work to the desired extent.

The aim of the invention is therefore to create a medical hand instrument that relieves the user.

SUMMARY OF THE INVENTION

According to the invention, this objective is achieved by a hand instrument of the type mentioned at the beginning, in which the handpiece is designed as a handle with three finger rests and a proximal support rest, the three finger rests being inclined to one another in such a way that the three finger rests extend in pairs at an angle of less than 90° between two finger rests to one another in a cross-section through the handpiece.

The invention includes the insight that an instrument currently available on the dental market for extracting bone chips from the jaw has the following deficits:

The handpiece is a straight rod. In use, this leads to fatigue of the dentist's fingers. The inventor has recognized that there is a lack of adequate shape and grip for the fingers and hand guidance to efficiently perform fine motor movements during ablation. Ablation is more of a feat of strength. The lack of ergonomics makes it difficult to use the instrument effectively in terms of ablation angle, posture angle and guide angle. The surrounding tissue can be and often is injured.

The instrument is based on the principle of scraping, which requires greater force for ablation with a lower yield. The scraping angle here is 160°. The cutting angle of the blade is not optimal and forces the dentist to use the instrument at a single defined angle. However, this is sometimes anatomically difficult and also leads to injury to soft tissue during scraping.

The scraping blade is not made of hardened spring steel and is far from being fully sharpened. It also dulls quickly.

The instrument is designed for right-handers only.

The chip chamber for holding the chips can only hold a volume of 2.5-3 $cm^3$.

The working surface is too large, which requires a larger surgical incision to be able to work into the donor area.

The ergonomic disposable bone scraper was developed from the inventor's practical experience to solve the aforementioned problems. Aspects of this medical hand instrument are as follows:

The shape of the instrument is based on ergonomic principles. The shape of the instrument allows fine motor movements of the user's fingers. Thanks to its ergonomic shape, the instrument sits comfortably in the hand and can therefore also be guided using fine motor skills.

Preferably, the finger rests are designed as depressions that are curved at least along the longitudinal direction of the instrument. The required stability and grip in the hand is achieved by means of recesses for the fingers and preferably additional nubs for grip. The recess on the underside is for support in the area between the thumb and index finger. Both right-handed and left-handed users have controlled guidance when working. This results in significantly less trauma to the soft tissue.

A preferred ablation angle of the scraping blade of 50° to 75° results from an imaginary line drawn through the handpiece in relation to the cutting edge at 18° to 25°. The scraping blade is located in the area of the scraping blade and chip pick-up gap, which is inclined at approx. 40° to the rest of the handpiece. This allows better fine motor control. However, these angles can also be easily adapted to the anatomical situation by changing the finger position in the recesses. The principle of scraping enables better ablation in terms of quality and quantity. The ablation angle corresponds to that of scraping and is between 50° and 75°. This also requires considerably less force, which relieves the surgeon's fingers and allows more fine motor skills.

The scraping blade is made of spring-hard steel and is noticeably sharper. This scraping blade hardly loses any of its sharpness when working.

In a preferred embodiment, the chip chamber can have a volume of more than 3.5 $cm^3$, preferably more than 4 $cm^3$. If, for example, the chip chamber can hold a volume of 4 $cm^3$, this also means less work interruption to empty the chip chamber compared to the prior art.

The working surface at the tip of the instrument is narrow—preferably 0.5 mm to 0.8 mm, e.g. 0.7 mm—and only 16 mm to 20 mm long, e.g. 18.9 mm. This results in more visibility during ablation, thus more control, guidance and no injury to soft tissue. Another advantage is that the surgeon needs a smaller surgical area, which means less cutting, less swelling and less pain. The attached figures and explanations illustrate what has been described.

Preferably, the three finger rests are designed as recesses and have a concave shape in the longitudinal direction of the handpiece.

The support rest is preferably formed by a convex surface at the proximal end of the handpiece, which is oriented in the radial direction of the handpiece in which an outer flat side of the scraping blade is oriented. It is particularly preferred if the support surface extends in the longitudinal direction of the hand instrument at an obtuse angle of between 0° and 10° in relation to the outer flat side of the scraping blade.

Preferably, the width of the handpiece in the area of the finger rests is between 11 mm and 16 mm. It is also preferable if the width of the handpiece is between 20 mm and 25 mm in the area of the support rest and initially decreases in the distal direction and increases again in the area of the finger rests.

The scraping blade preferably extends essentially, in particular with the exception of the cutting edge, in a blade plane that is inclined by at least 50° in relation to the longitudinal axis of the handpiece.

The handpiece is preferably made of thermoplastic material, preferably polycarbonate or polyamide approved for medical use, for example the polycarbonate Makrolon 2458 or the polyamide ixef 1022.

Preferably, the chip chamber and the handpiece are formed in one piece and are part of a one-piece base body to which the scraping blade and a chip chamber lock in the form of a removable cover are attached.

According to an embodiment of the hand instrument, the scraping blade is designed as a conical disk and is attached to a shaft that is longitudinally displaceable in the handpiece. The circumferential edge of the conical disk forms the cutting edge of the scraping blade. The cutting edge angle of the scraping blade is also defined by the conical shape of the scraping blade.

In this embodiment, the chip chamber is preferably designed as a cylindrical cavity concentrically surrounding the shaft, which is open at the distal end of the handpiece. Scraping chips can be ejected distally from the chip chamber by means of an ejector preferably provided. For this purpose, the ejector is arranged in the handpiece together with the scraping blade and the shaft so that it can move longitudinally. The ejector has an axial distance from the scraping blade and the chip chamber extends in the axial direction between the scraping blade and an end wall of the ejector.

Preferably, the shaft with the scraping blade can be locked in such a way that the shaft and the scraping blade (in the locked state) are no longer longitudinally displaceable with respect to the handpiece and the scraping blade is locked in a working position used for scraping in such a way that tensile forces can be introduced into the shaft by means of the handpiece and transmitted to the scraping blade.

The shaft is preferably connected at least indirectly to a handle, which serves to move the shaft and the scraping blade longitudinally in relation to the handpiece. The handpiece preferably has a longitudinal groove for guiding the handle. In addition, the handpiece preferably has a recess at the proximal end of the longitudinal groove, into which the handle can be pivoted by means of a rotary movement around the longitudinal axis of the shaft in order to lock the shaft and the scraping blade in the working position.

In a hand instrument with a scraping blade in the form of a conical disk or a blunt cone, the distal end of the handpiece, in particular of the base body of the handpiece, has a stepped shape, with a distally forward-projecting protrusion of the base body enclosing a first circumferential portion of the scraping blade, while an end wall of the base body that is recessed in the longitudinal direction of the base body longitudinally delimits the gap that leads to the chip chamber. The gap is thus located between the cutting edge of the scraping blade and the end wall of the base body of the hand instrument, which is set back in the axial direction. In the region of the first circumferential portion of the scraping blade, a support and contact surface for the scraping blade is also preferably provided at the distal end of the base body, which support and contact surface lies in a plane extending perpendicular to the longitudinal axis of the shaft of the scraping blade, which plane is offset in the distal direction by the width of the gap with respect to the plane in which the end face delimiting the gap extends. The support and contact surface is preferably bordered by the forwardly projecting protrusion of the base body.

During scraping, tensile forces act in the shank of the scraping blade and are transferred to the scraping blade. The material to be scraped exerts forces on the scraping blade in the opposite direction to the tensile force, resulting in a torque. The support and contact surface at the distal end of the base body absorbs this torque and supports the scraping blade. The protrusion of the base body projecting forwards absorbs forces acting on the scraping blade transversely to the longitudinal axis of the shaft. The shank, the support and contact surface and the forward projecting protrusion of the base body optimally stabilize the scraping blade in its working position for scraping and hold it in such a way that the forces acting during scraping are transferred to the base body without the shank and scraping blade becoming more deformed under the influence of the acting forces. The risk of injury is also reduced by the protrusion at the distal end of the base body, which encompasses the first circumferential portion of the cutting edge in the working position of the scraping blade.

The ergonomic shape of the handpiece and the design of the scraping blade and the distal end of the base body have a synergistic effect and, in combination with each other, allow particularly precise and effective handling of the instrument, because the gripping surfaces on the base body allow precise introduction of hand and finger forces into the instrument and the design of the scraping blade in combination with the design of the distal end of the base body allows precise implementation of the forces introduced.

BRIEF DESCRIPTION OF THE DRAWINGS

The invention will now be explained in more detail by means of an embodiment example with reference to the figures. The figures show.

DETAILED DESCRIPTION

Figure 1:
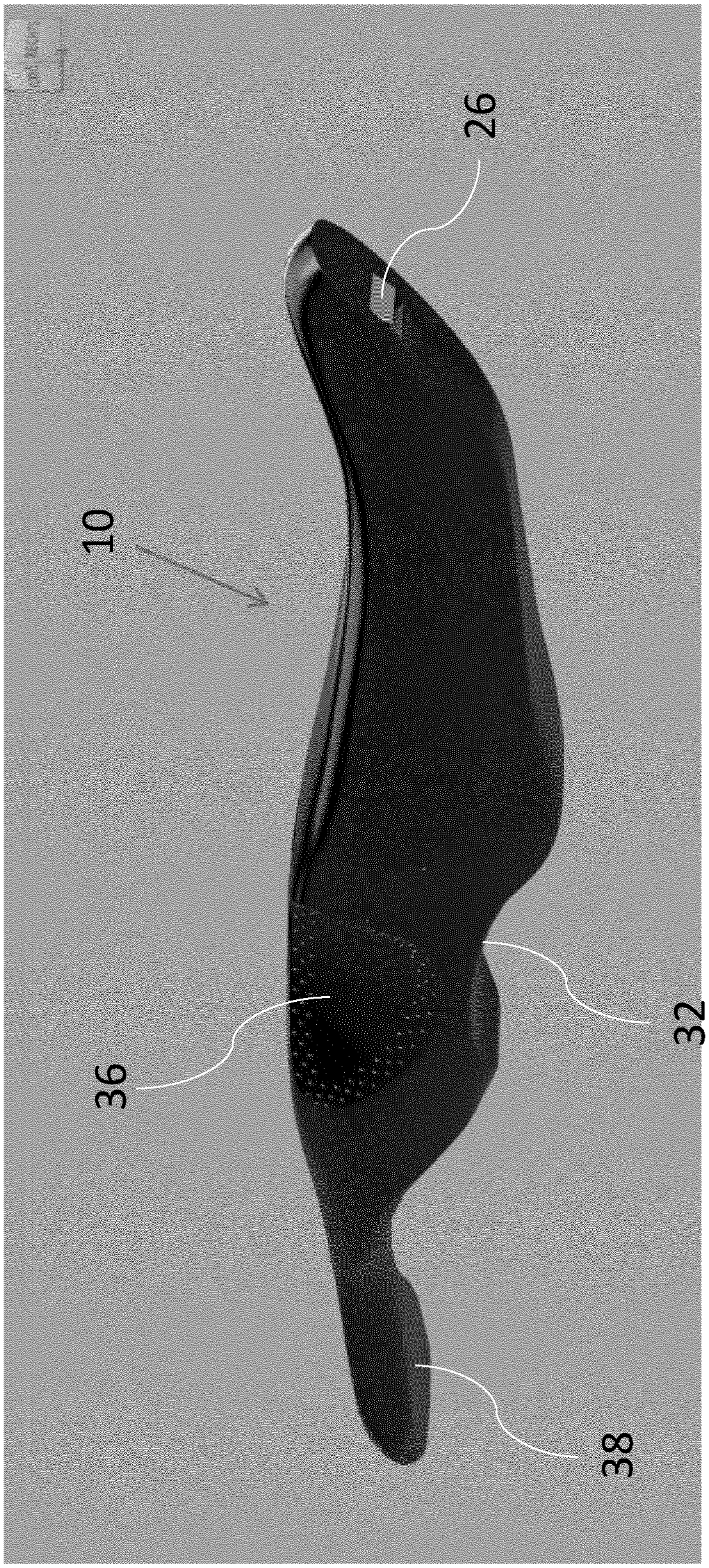
FIG. 1: a perspective view of the medical hand instrument.

A medical hand instrument 10 according to the invention has a preferably integrally formed base body 12, which extends from a distal end 14 of the medical hand instrument 10 to a proximal end 16 of the medical hand instrument. Close to its distal end 14, the medical hand instrument has a scraping blade 18. A longitudinal section of the one-piece base body 12 extending proximally of the scraping blade 18 is formed as a handpiece 20. The handpiece 20 is used for gripping the medical hand instrument 10 with one hand.

Two embodiments of the medical hand instrument 10 are presented. FIGS. 1 to 20 show a first variant as well as sub-variants of the first variant of the medical hand instrument 10 and details thereof, while FIGS. 21 to 29 show a second variant of the medical hand instrument 10 and details thereof.

The differences relate in particular to the scraping blade, while the longitudinal section of the one-piece base body 12 designed as the handpiece 20 is at least similar in both embodiments.

First, the first variant of the medical hand instrument 10 is described in more detail:

The handpiece 20 extends along a longitudinal axis 22 and the scraping blade 18 extends in a blade plane 24. The cutting edge 26 of the scraping blade 18 protrudes from the blade plane 24, so that a cutting angle 28 is formed between the cutting edge 26 and the blade plane 24.

Preferably, the ablation angle of the scraping blade is between 50° and 75° and the guide angle is preferably about 40°. The ablation angle $\alpha+\beta$ of the scraping blade between 50° and 75° results from the position of the cutting edge 26 with the cutting angle $\alpha$ of 18° and a horizontally drawn line through the entire handpiece 20. The guide angle $\beta$, which should be approximately 40°, results from the inclination of the scraping blade and gap surrounding the area for receiving the chips (corresponding to the blade plane 24) in relation to the handpiece 20. The guide angle $\beta$ is thus the inclination of the tip of the instrument in relation to the rest of the instrument 10.

A chip chamber 30 adjoins the scraping blade 18, so that bone chips scraped off the cutting edge 26 of the scraping blade 18 enter the chip chamber 30. The chip chamber 30 has a volume of approximately 4 $cm^3$. The chip chamber 30 is provided with a removable cover 40; see FIGS. 9 and 10.

The handpiece 20 has three finger rests 32, 34 and 36 in the form of recesses. A finger rest 32 for the middle finger of a user is located on the same side of the medical hand instrument 10 as the scraping blade 18. A finger rest 34 for the thumb of the user and a finger rest 36 for the index finger of the user are arranged on the side of the handpiece 20 of the medical hand instrument 10. In the cross-section of the handpiece 20 (see FIG. 8), it can be seen that the finger rests are arranged in cross-section in such a way that they each form an angle of less than 90° between them.

In the longitudinal direction 22 of the handpiece 20, the finger rests 32, 34 and 36 are groove-shaped, i.e. concavely curved. As a result, the finger rests 32, 34 and 36 each provide good support for the respective adjacent finger of the user. At the proximal end 16 of the hand instrument 10, the handpiece 20 is flat and relatively wide in shape and thus forms a proximal support rest 38 which, when the medical hand instrument 10 is used, can rest the finger root area between the thumb and index finger of the user on the user's hand, so that the user can easily apply the pressure force required for scraping and the corresponding counterforce is transmitted to the user's hand via the relatively large surface of the support rest.

Figure 2:
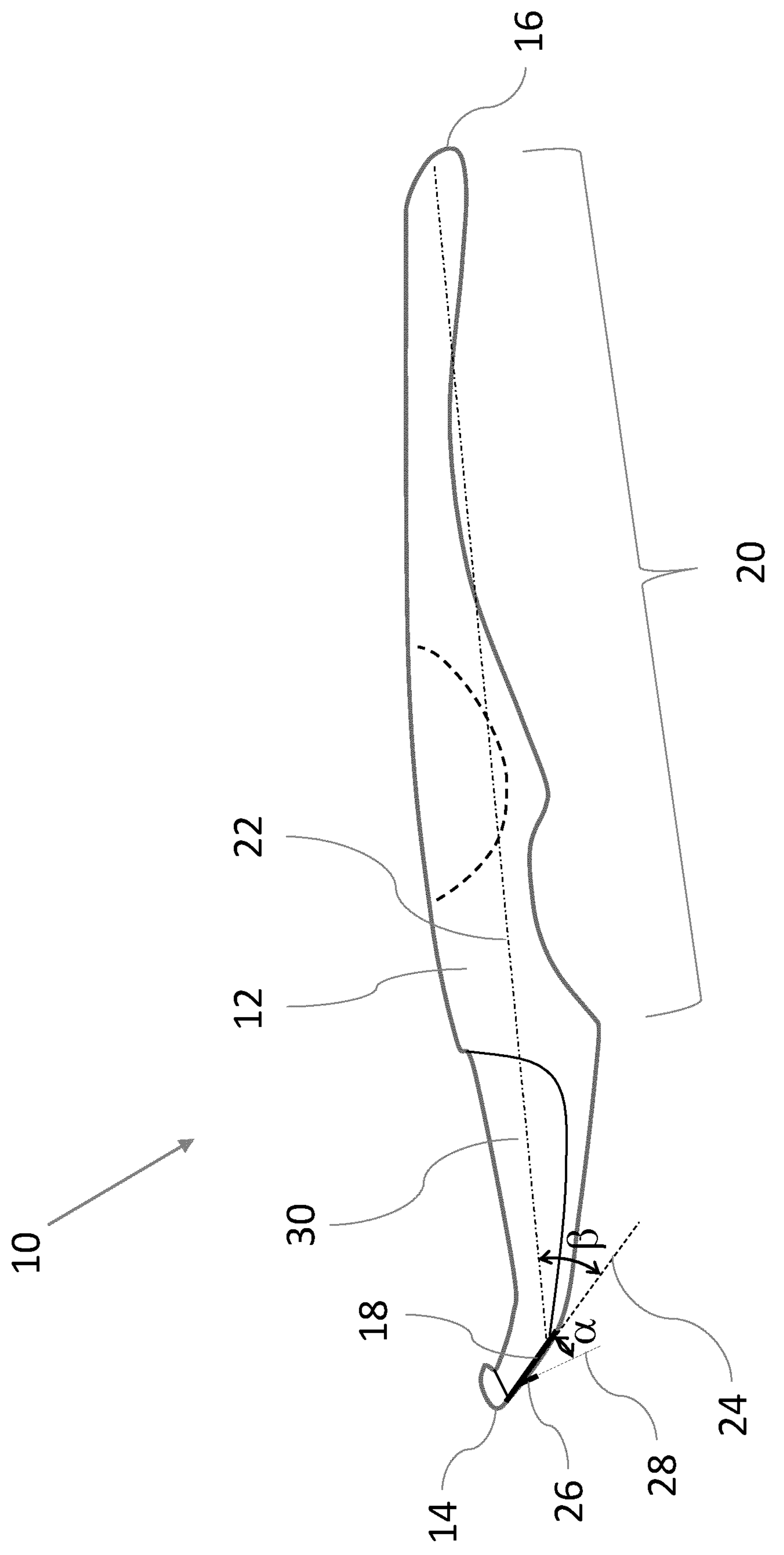
FIG. 2: a longitudinal section through the medical hand instrument.
Figure 3:
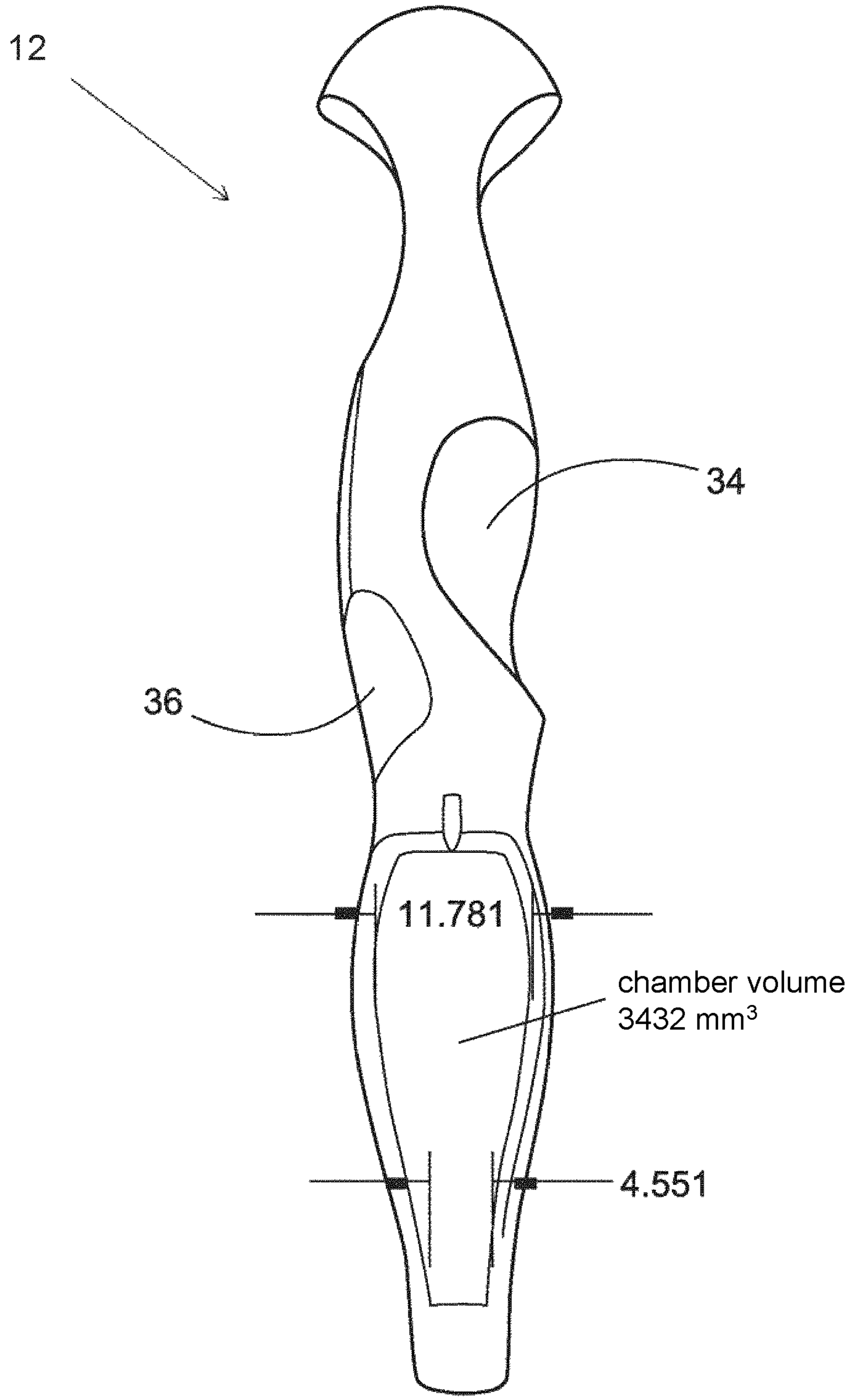
FIG. 3: a view of the medical hand instrument from the front and diagonally above.
Figure 4:
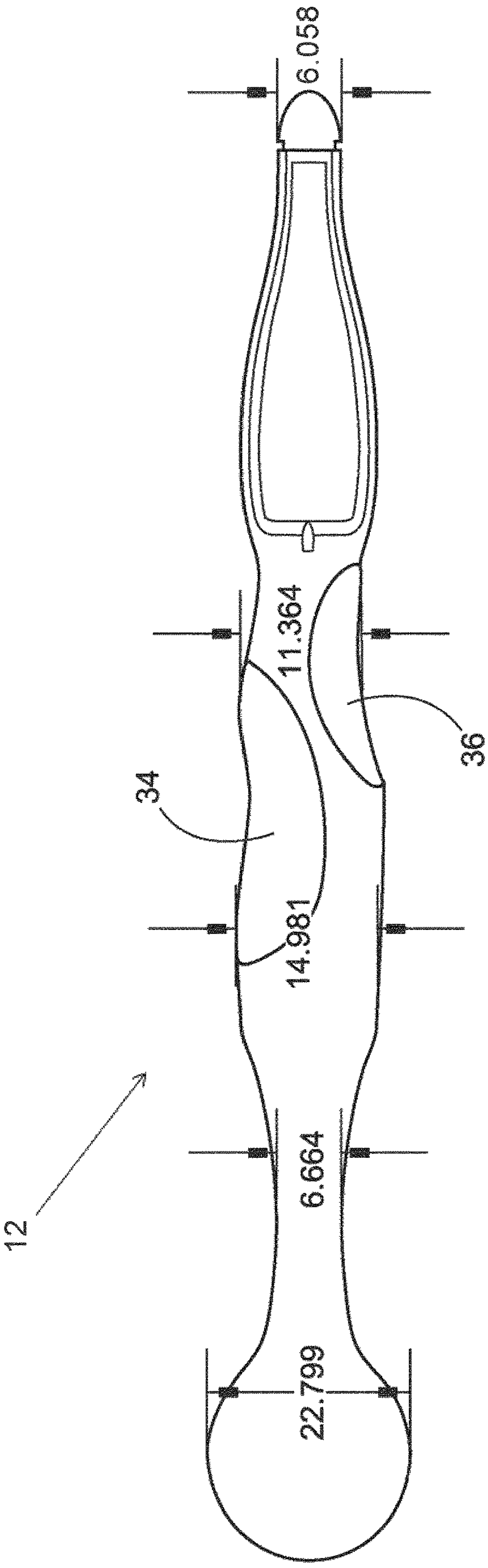
FIG. 4: a view of the medical hand instrument.
Figure 5:
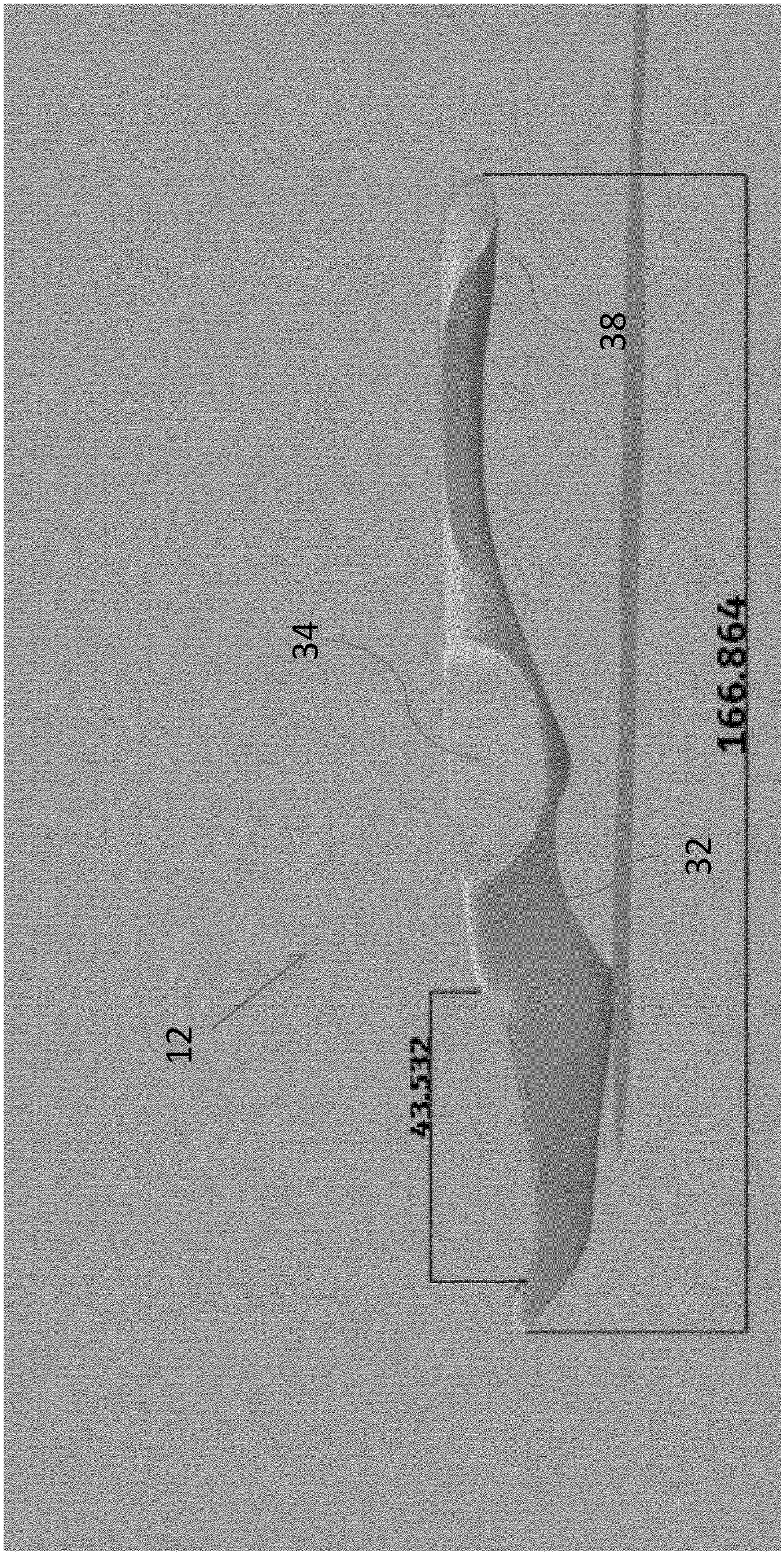
FIG. 5: a left side view of the medical hand instrument.
Figure 6:
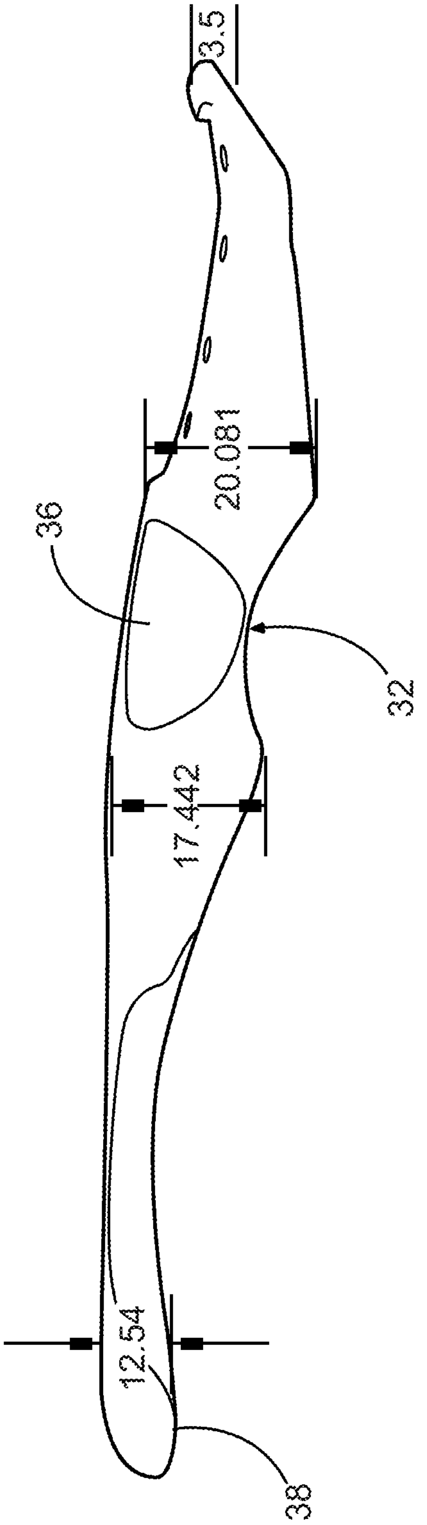
FIG. 6: a right side view of the medical hand instrument.
Figure 7:
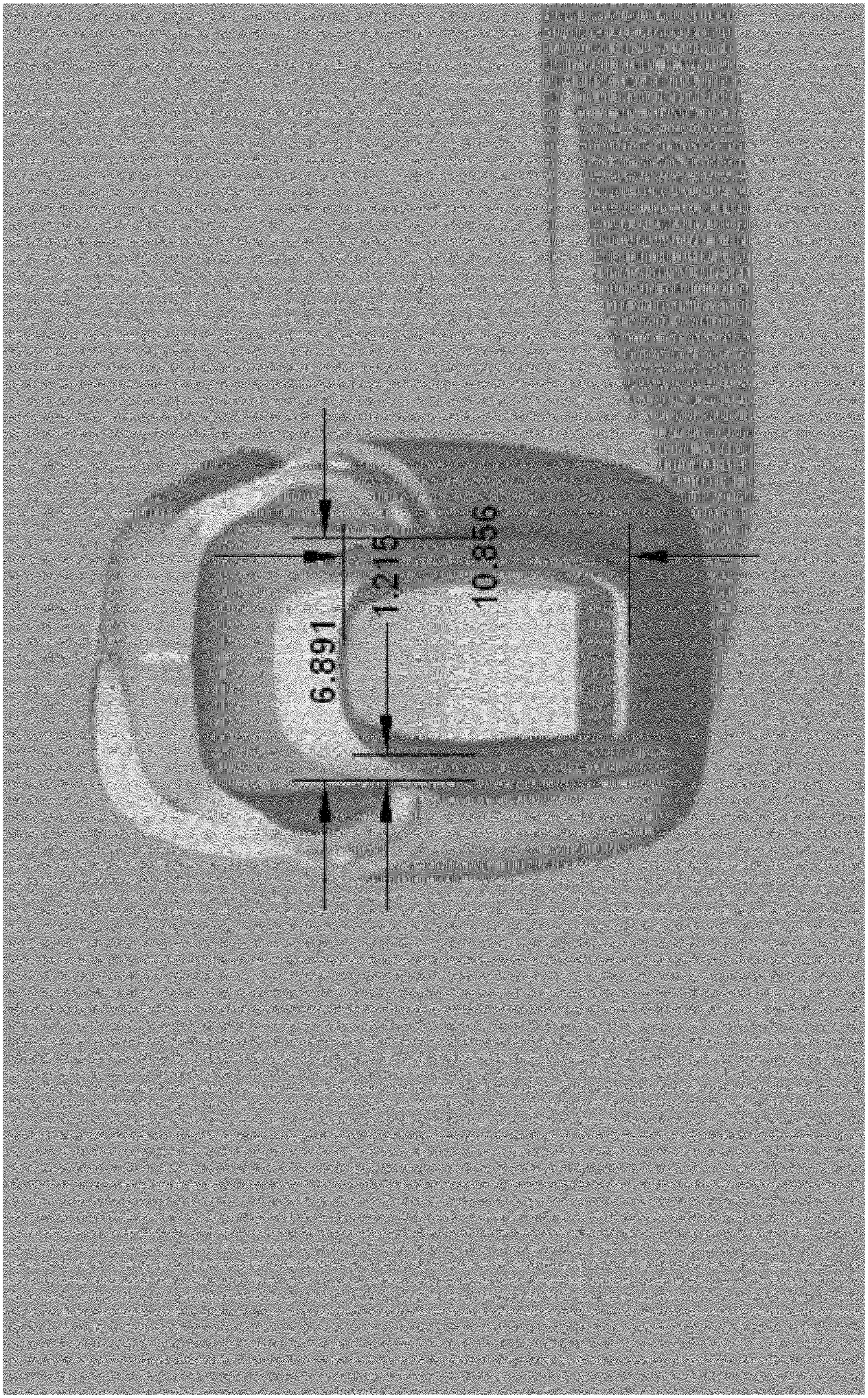
FIG. 7: a front view of the medical hand instrument.
Figure 8:
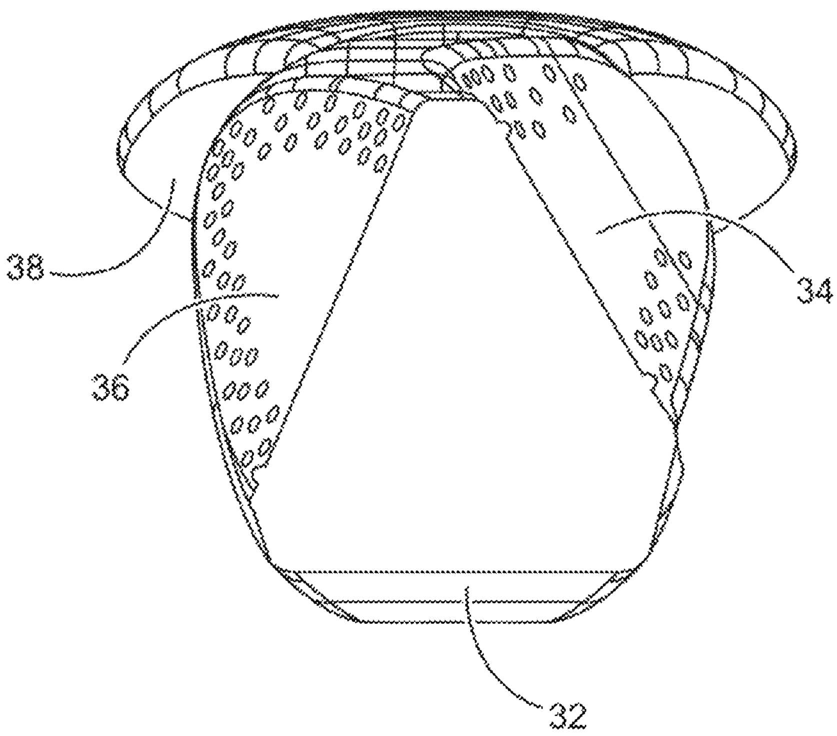
FIG. 8: a cross-section through the medical hand instrument in the area of the finger rests

FIGS. 1 and 2 show the base body 12 with attached scraping blade 18 of a first embodiment of the medical hand instrument 10. The one-piece base body 12 of this embodiment is shown again in different views in FIGS. 3 to 7. The base body 12 is preferably injection-molded from a plastic, in particular a polyamide or a polycarbonate.

Figure 9:
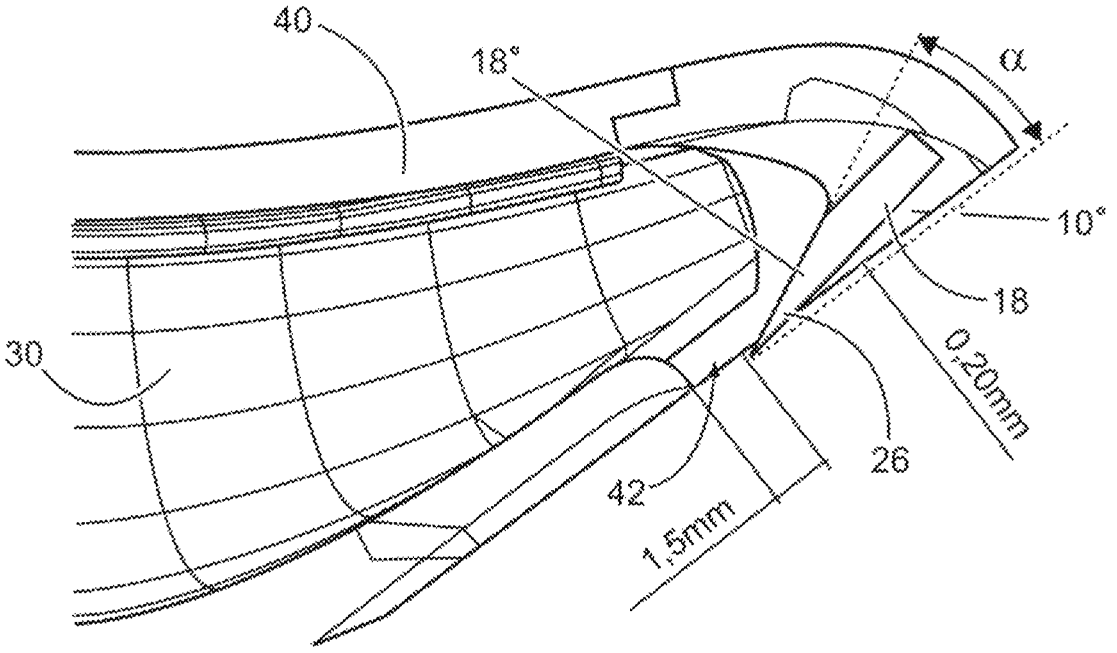
FIG. 9: details of the instrument tip in a partially sectioned side view.
Figure 10:
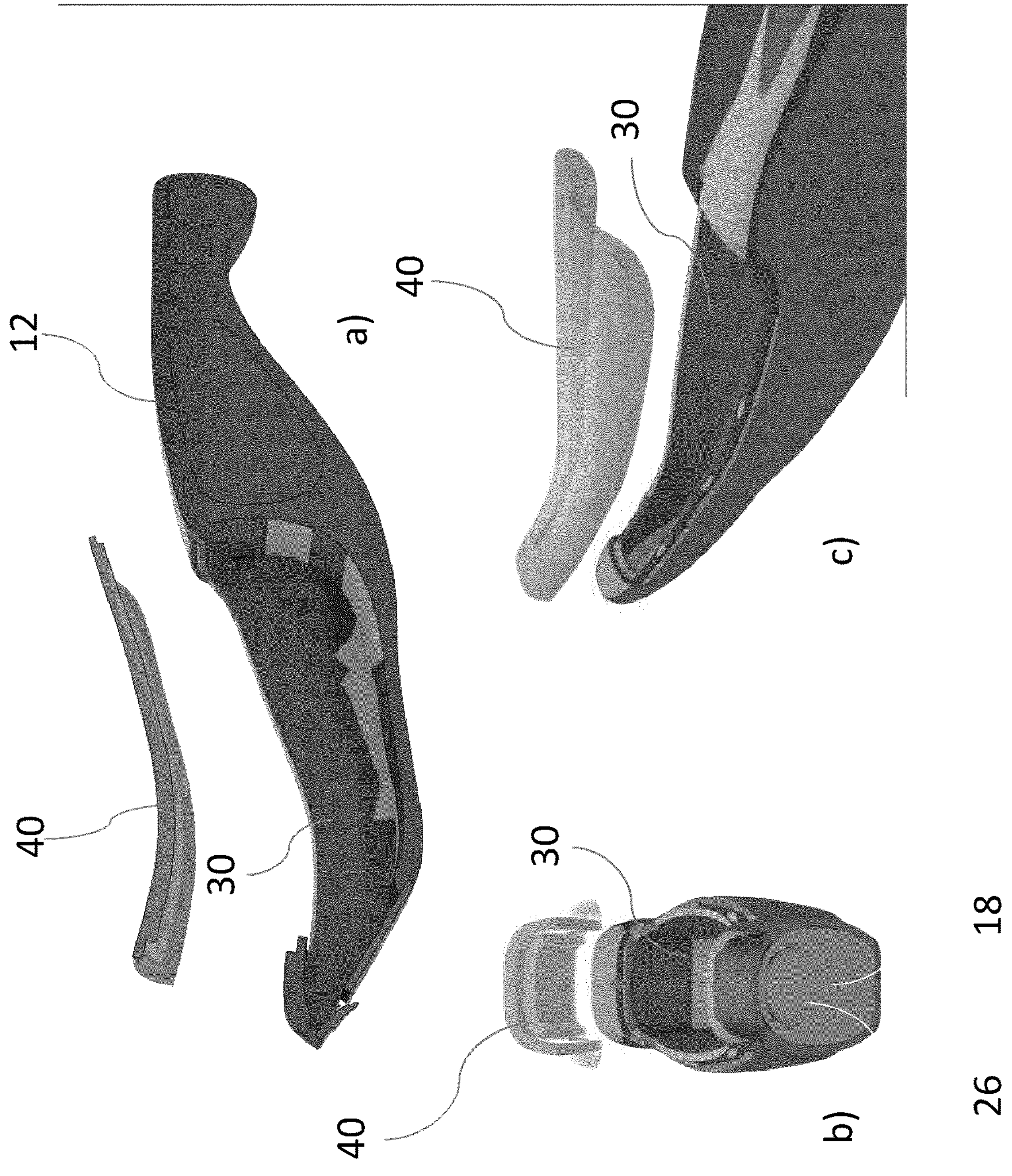
FIGS. 10*a-c*: various perspective views illustrating the chip chamber of the hand instrument.

FIG. 9 shows embodiment details of the tip of the instrument 10 with the scraping blade 18 and the chip chamber 30 as well as the cover 40. Immediately adjacent to the cutting edge 26 of the scraping blade 18 is a gap 42 through which the bone chips scraped off by the scraping blade 18 can enter the chip chamber 30. As shown in FIG. 9, the scraping blade 18 may be embedded at an angle in, for example, plastic. In particular, a scraping blade 18 made of stainless steel can be encapsulated by thermoplastic material. Alternatively, the cutting edge 26 of the scraping blade 18 can also be bent out of a larger piece of sheet metal, in which case the sheet metal forms the blade plane 24 (see FIG. 2).

FIGS. 10*a* to 10*c* illustrate in partially sectioned and perspective views how the chip chamber 30 can be closed with the cover and how the scraping blade 18 can be formed by a piece of sheet metal from which the actual cutting edge 26 is bent out, similar to what is known, for example, from kitchen graters.

Figure 11:
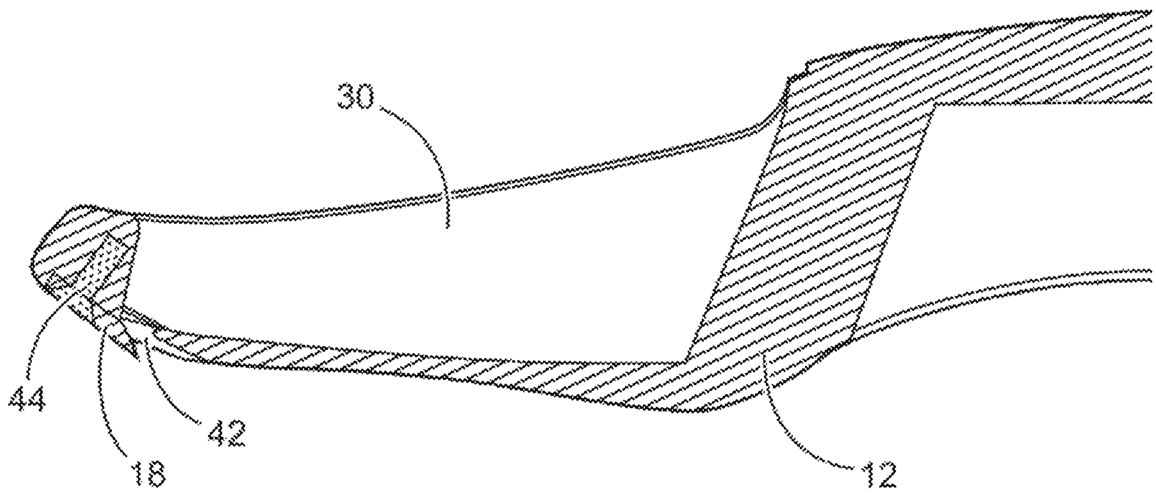
FIG. 11: a longitudinal section through a distal end section of the medical hand instrument to illustrate the arrangement of the scraping blade and chip chamber.

FIG. 11 shows a longitudinal section through a distal end section of the base body 12 of a further embodiment of the hand instrument 10. The chip chamber 30 is located in the illustrated distal longitudinal section. In addition, near the distal end of the hand instrument 10, the scraping blade 18 is attached to the base body 12 by means of a screw 44. The gap 42, through which bone chips separated from the cutting edge 26 of the scraping blade 18 can enter the chip chamber 30, can also be seen. The embodiment variant illustrated in FIG. 11 for the attachment of the scraping blade 18 to the base body 12 differs from the variant illustrated in FIG. 9 in particular in that the scraping blade 18 is attached to the base body 12 of the hand instrument 10 by means of the screw 44.

Figure 12:
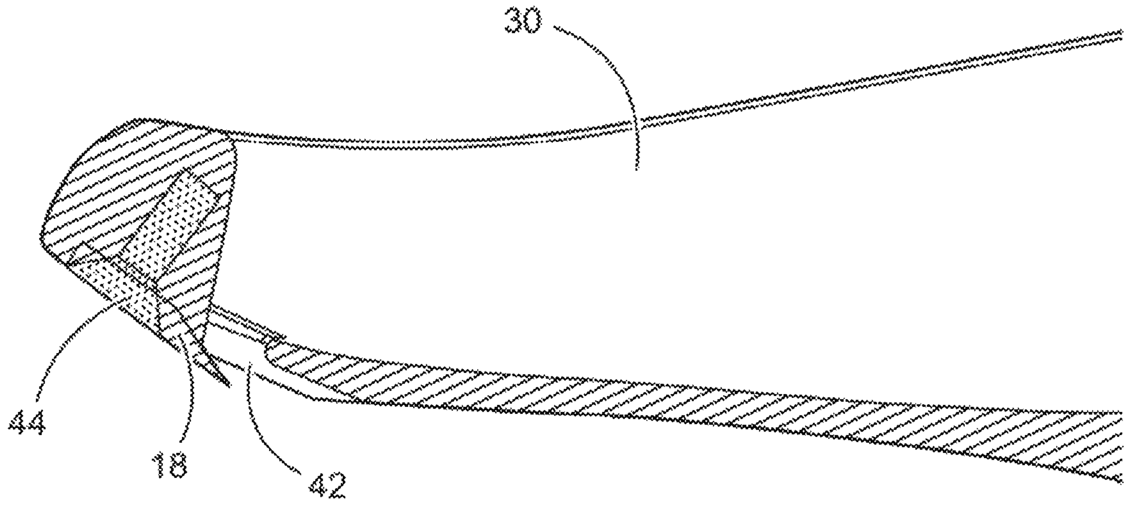
FIG. 12: an enlarged section of the longitudinal section from FIG. 11.

This can be seen even more clearly in the enlarged illustration in FIG. 12.

Figure 13:
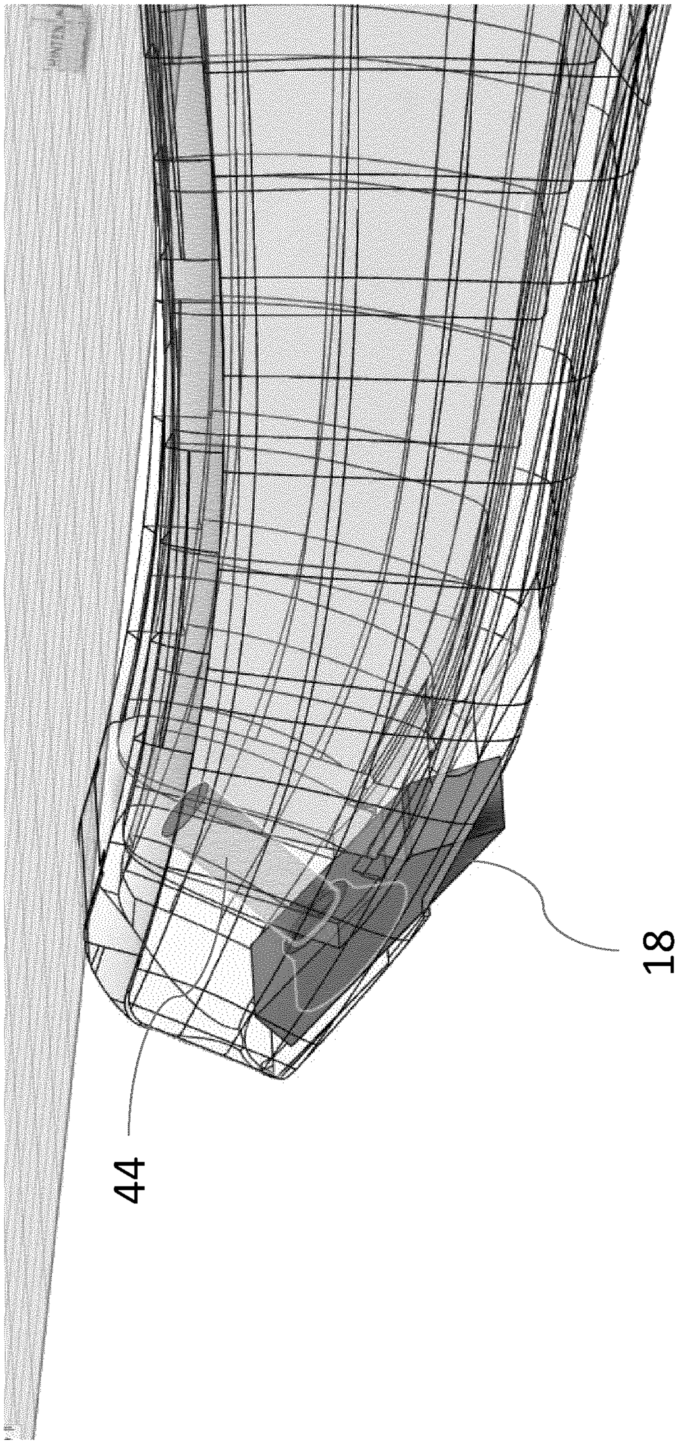
FIG. 13: a grid model of a distal longitudinal section of the hand instrument to show the spatial arrangement of the scraping blade and a fastening screw for the scraping blade.

FIG. 13 shows a grid model of the main body 12 of the hand instrument 10 and the scraping blade 18 and the screw 44 in a perspective view illustrating the spatial arrangement of the scraping blade 18 and the screw 44 with respect to the distal end of the main body 12 of the hand instrument 10.

Figure 16:
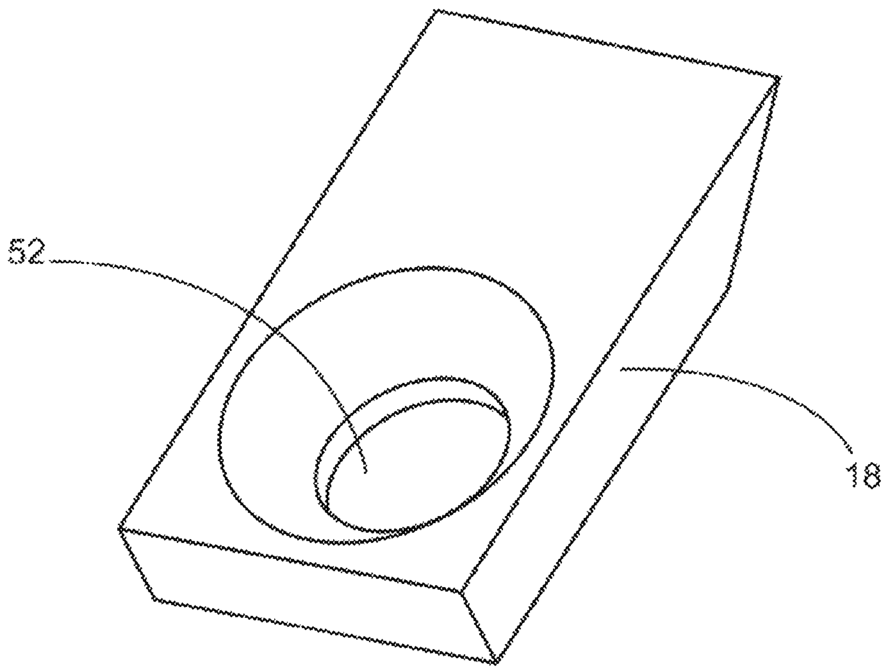
FIG. 16: a perspective view of the scraping blade.
Figure 17:
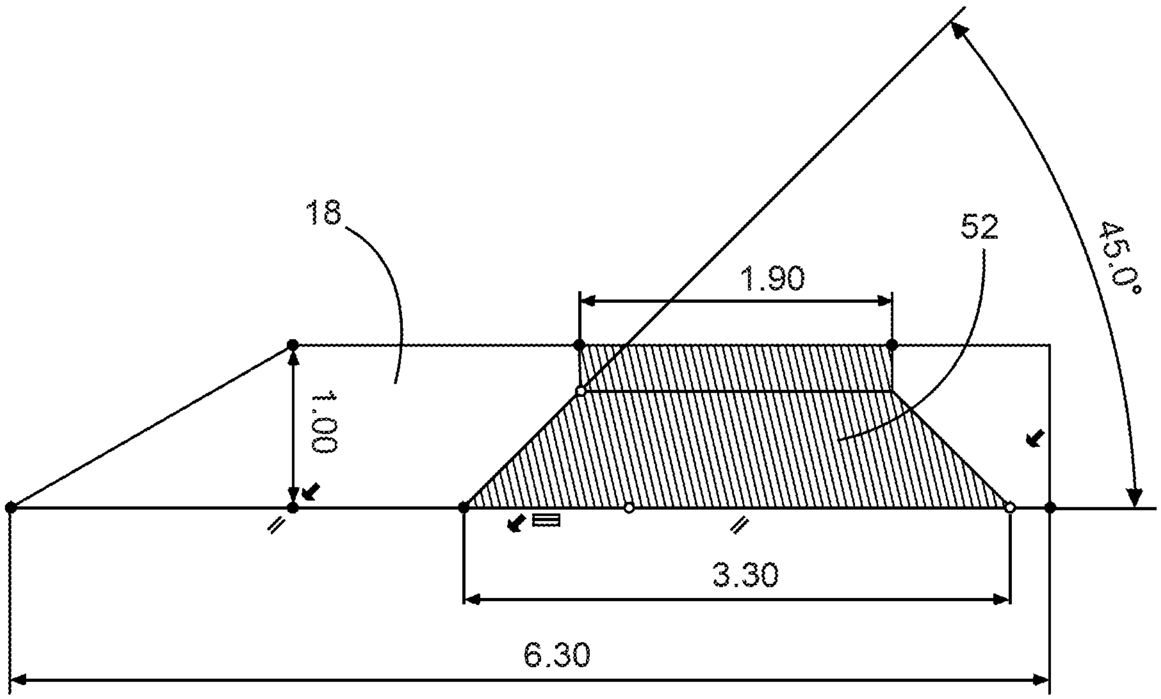
FIG. 17: a schematic longitudinal section through the scraping blade.
Figure 18:
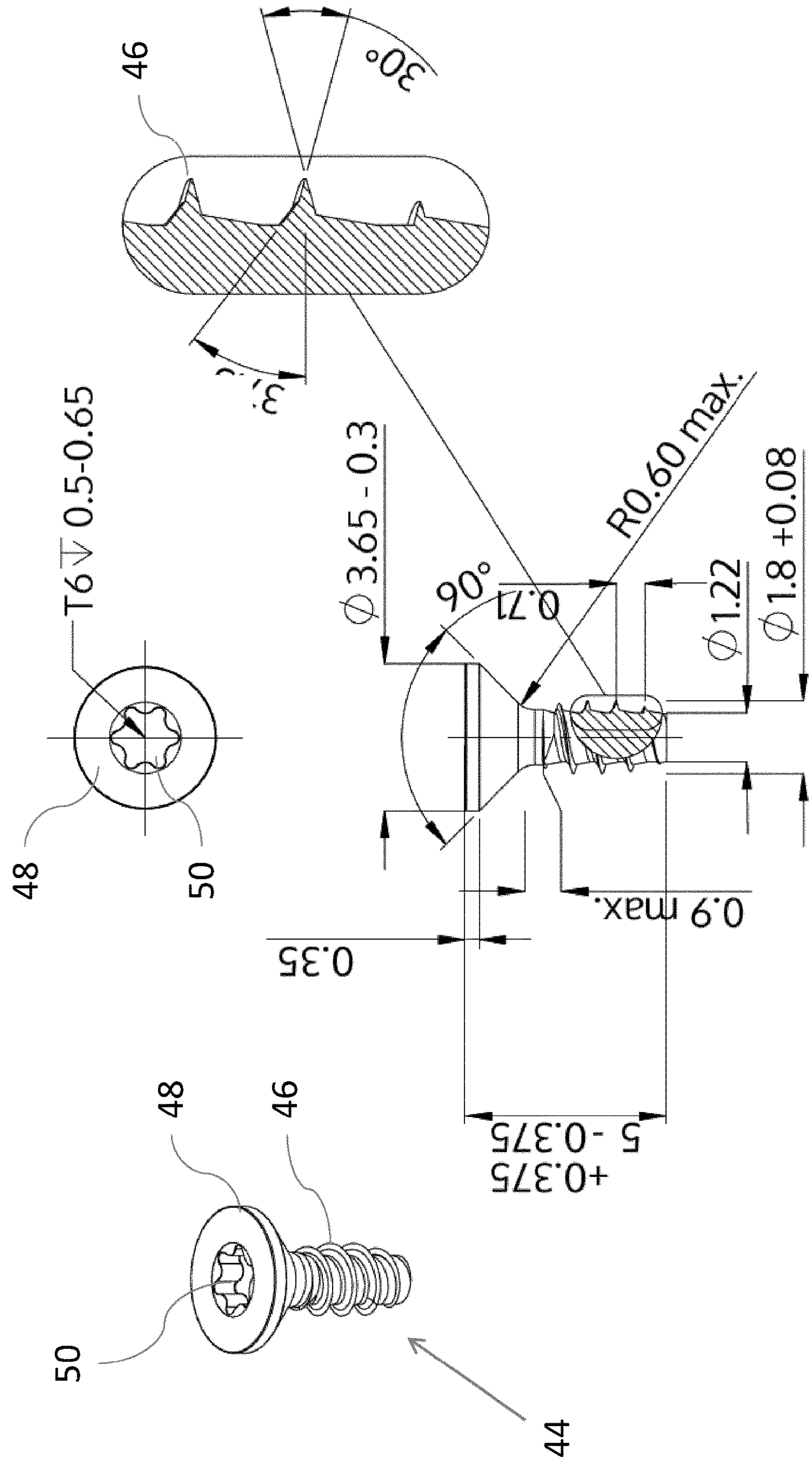
FIG. 18: various views of the fixing screw for attaching the scraping blade to the hand instrument.

FIG. 16 shows a perspective view of the scraping blade 18 and FIG. 17 shows a longitudinal section through the scraping blade 18.

As can be seen from FIGS. 11 to 13, in the embodiment shown there it is provided that the scraping blade 18 is attached to the base body 12 of the hand instrument 10 by means of the screw 44. As a result, the scraping blade 18 is basically detachably connected to the rest of the hand instrument 10. However, an important aspect is that the fastening of the scraping blade 18 by means of the screw 44 ensures that the scraping blade 18 is fastened firmly enough to the base body 12 of the hand instrument 10.

Figure 14:
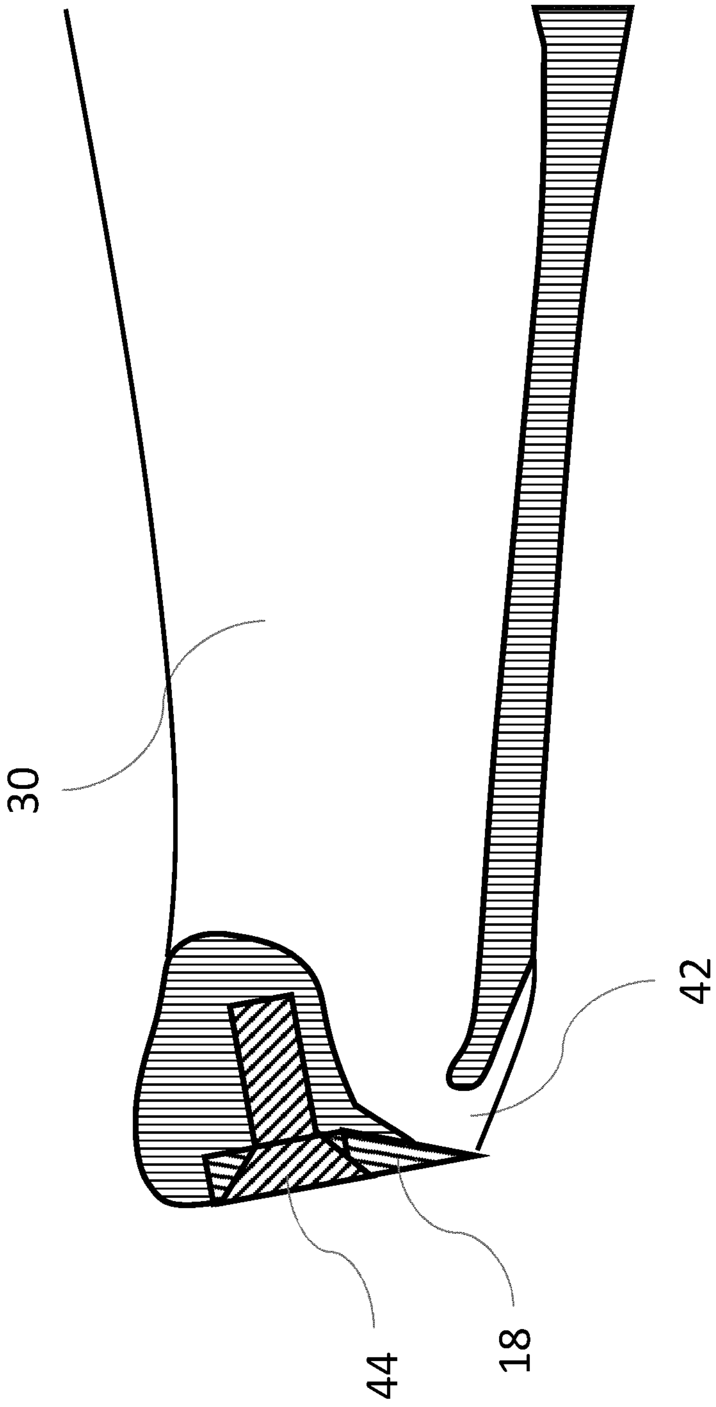
FIG. 14: an alternative embodiment of a hand-held medical device similar to the one shown above, but with a larger angle between the blade plane and the longitudinal axis of the handpiece.
Figure 15:
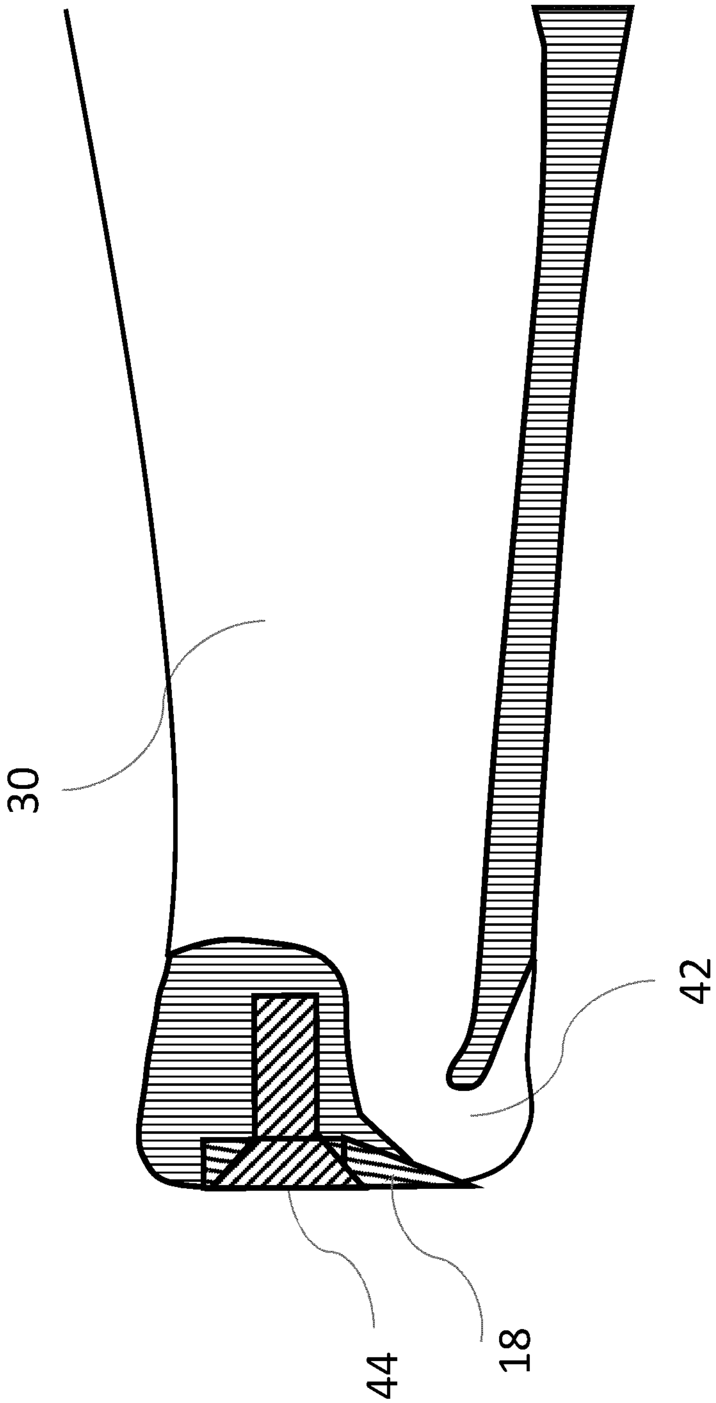
FIG. 15: another alternative embodiment of a medical handpiece similar to the one shown above, but with an even larger angle between the blade plane and the longitudinal axis of the handpiece.

Different embodiments of the hand instrument 10 may differ in the angle at which the blade plane 24 extends relative to the longitudinal axis 22 of the handpiece 20. FIGS. 14 and 15 illustrate two examples in which the angle between the blade plane 24 and the longitudinal axis 22 of the handpiece 20 is greater than in the examples illustrated in FIGS. 1 to 13, namely up to 90° (see FIG. 15).

This also depends on the geometry of the screw 44, which is shown in detail in FIG. 16. As can be seen, the screw 44 has a self-tapping thread 46 and a countersunk head 48. A recess 50 with a driver profile in the form of a hexalobular socket is provided in the countersunk head 48 in order to be able to turn the screw 44 using a corresponding tool of size T6. The outer diameter of the countersunk head 48 is dimensioned such that it extends over almost the entire width of the scraping blade 18 in order to ensure the largest possible contact surface between the bevels of the countersunk head 48, the screw 44 and the corresponding bevels of the associated fastening opening 52 in the scraping blade 18. The fastening opening 52 is designed in such a way that the countersunk head (screw head) 48 of the screw 44 does not protrude beyond the contour of the scraping blade 18 when the scraping blade 18 is screwed to the base body 12 of the hand instrument 10 by means of the screw 44. This is shown, for example, in FIG. 12.

The illustrated fastening of the scraping blade 18 by means of the screw 44 offers two advantages. Due to the advantageous design of the scraping blade 18 and screw 44, the attachment of the scraping blade 18 to the base body 12 by means of the screw 44 is particularly firm. Since the screw 44 has a self-tapping thread 46, the base body 12 of the hand instrument 10 can easily be produced from a thermoplastic material by injection molding without also having to produce a thread for the screw 44. A further advantage is that it is theoretically possible to replace a possibly blunt scraping blade 18 with a new scraping blade 18 during the treatment of a patient. In principle, however, the hand instrument 10 is intended for single use, in which the scraping blade 18 remains permanently connected to the base body 12 and is disposed of together with the rest of the hand instrument 10 after the hand instrument has been used on a patient.

Figure 19:
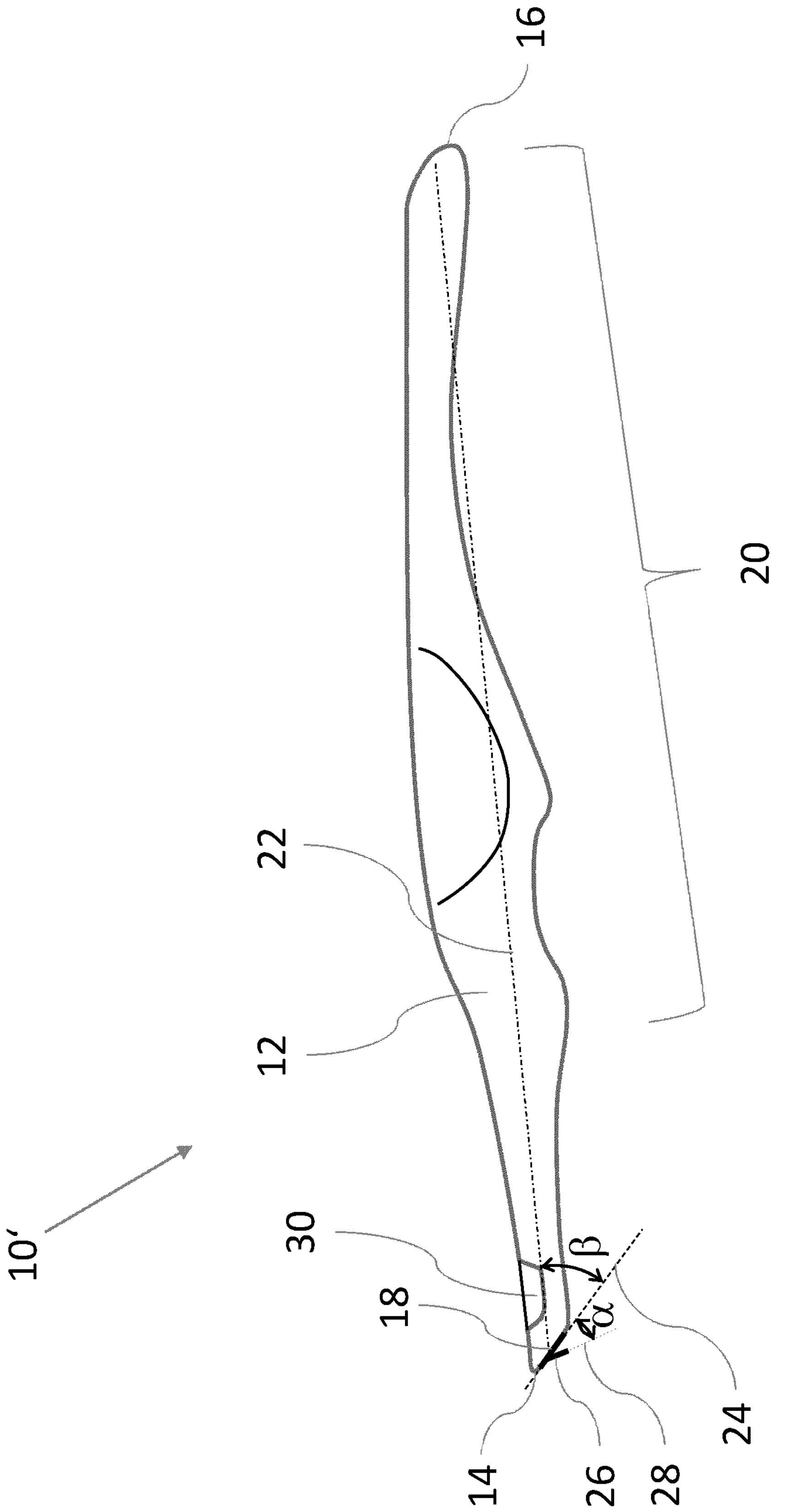
FIG. 19: an alternative embodiment of a hand-held medical device similar to that shown above but with a narrower distal end.

Depending on the patient, a medical hand instrument as shown in FIGS. 1 to 13 may be too large. For this reason, the medical hand instrument 10' can alternatively be designed so that its entire distal area, including the scraping blade 26' and the chip chamber 30', is much narrower. Such a medical hand instrument 10' is illustrated in FIG. 19.

Figure 20:
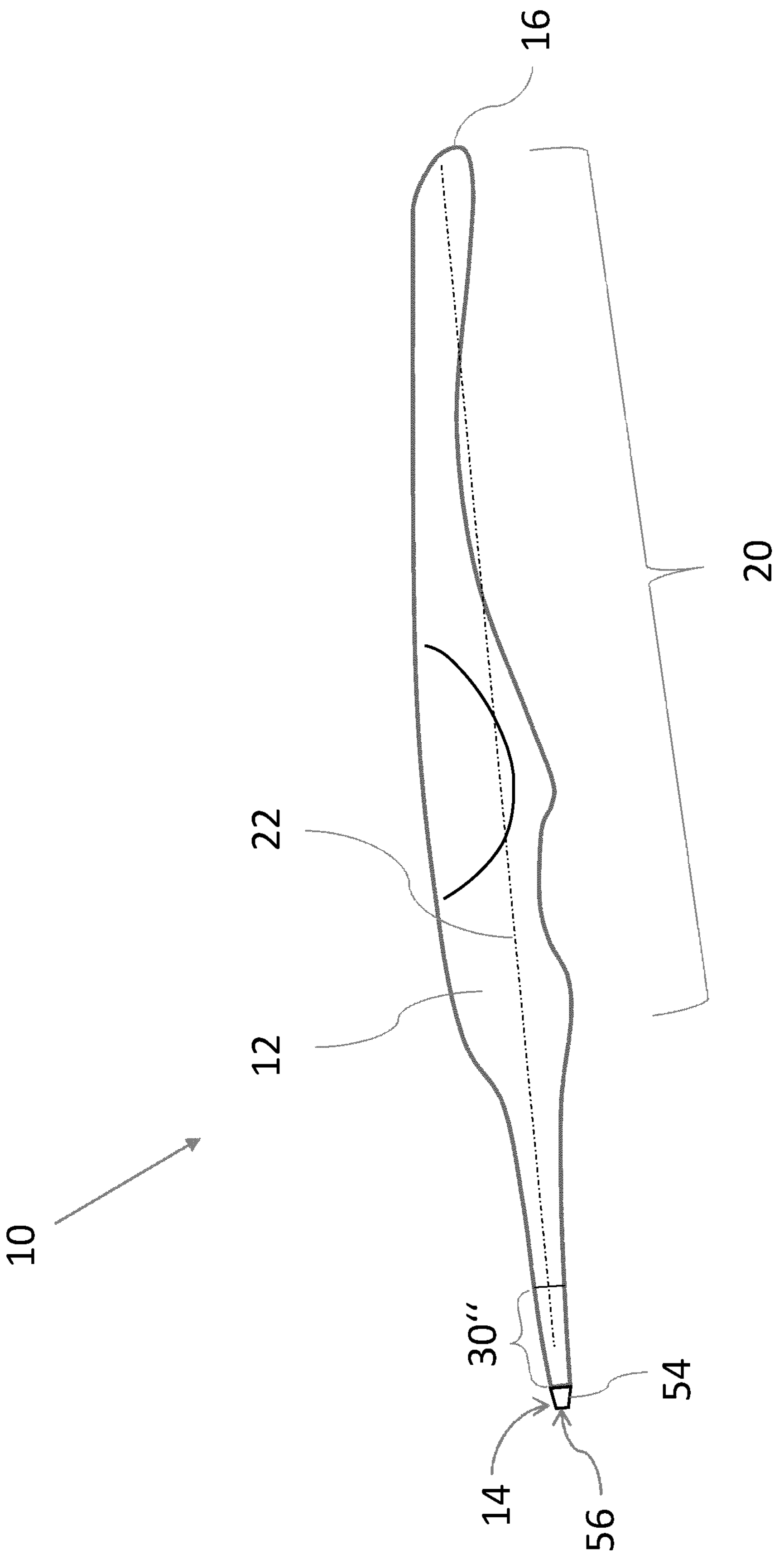
FIG. 20: another alternative embodiment of the medical hand instrument with a round blade attached to a chip chamber that can be removed from the rest of the hand instrument.
Figure 21:
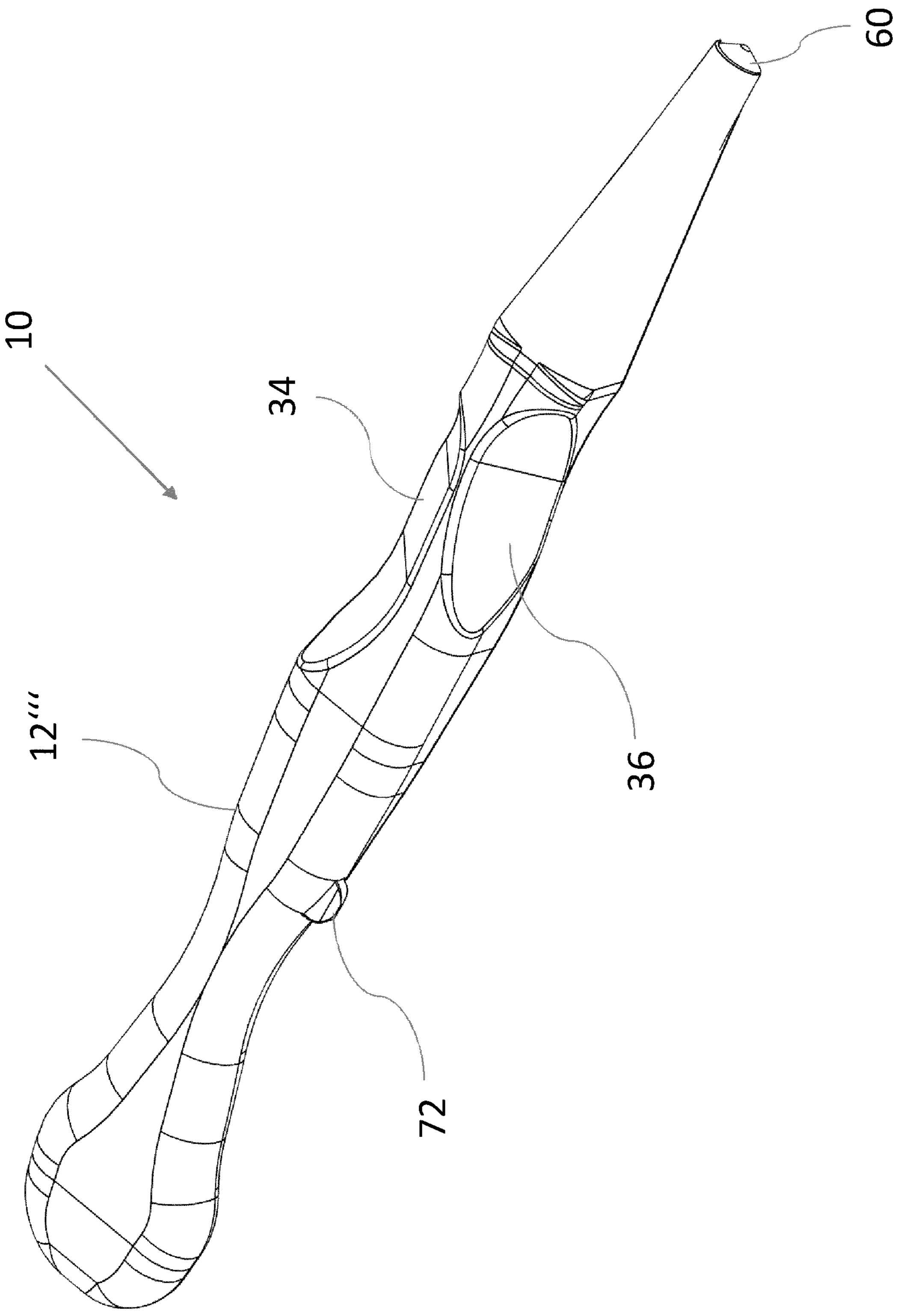
FIG. 21: a perspective view of a second variant of the medical hand instrument from above.
Figure 22:
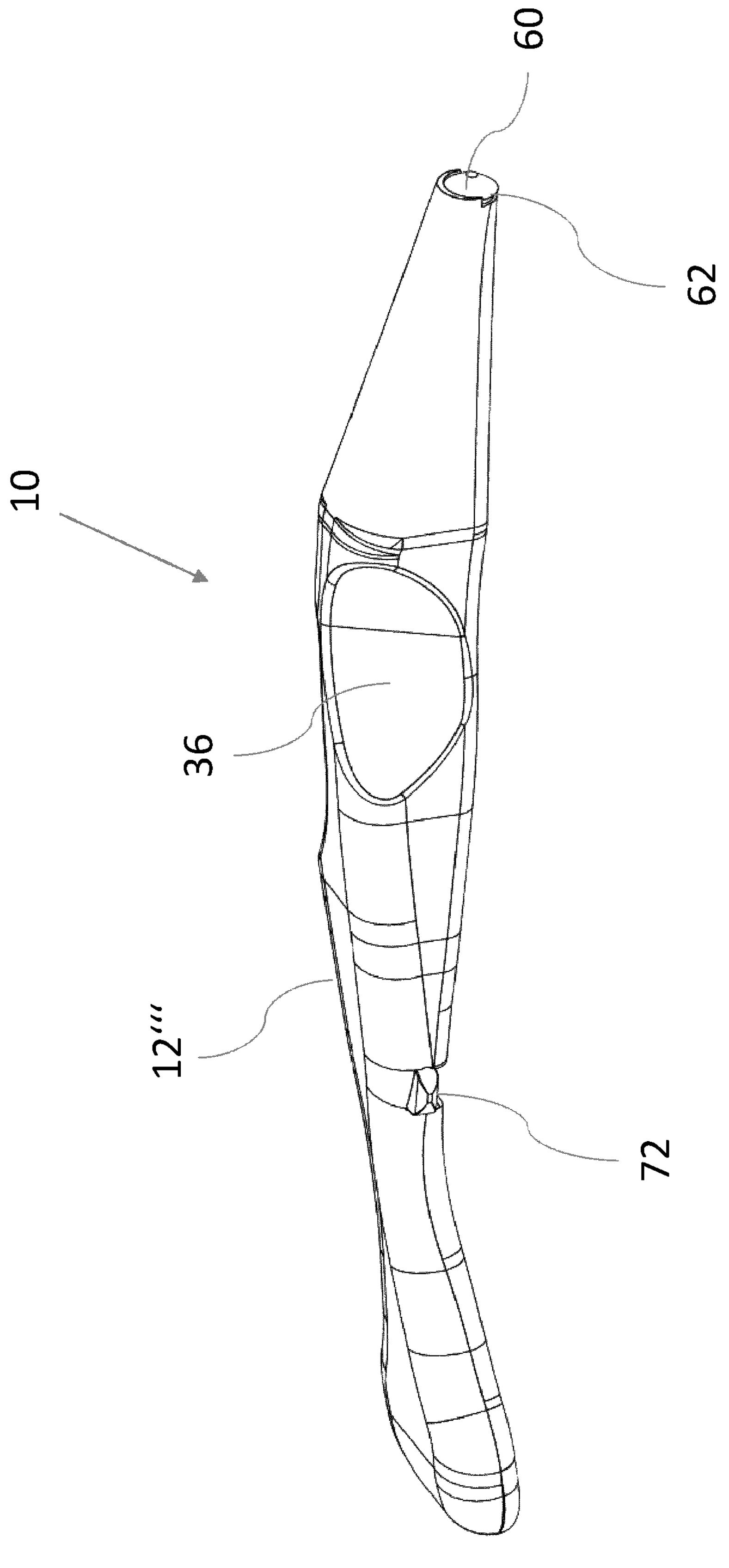
FIG. 22: a perspective view of the second variant of the medical hand instrument from the side.

According to a sub-variant of the first variant of the medical hand instrument 10", the medical hand instrument 10'" has a ring blade 54 at its distal end which is attached to a distal end of a sleeve-shaped chip chamber 30"; see FIG. 20. The ring-shaped scraping blade 54 encloses a central opening 56 through which scraped bone chips can pass into the chip chamber 30".

The sleeve-shaped chip chamber 30" together with the ring blade 54 attached to it can be separated from the rest of the medical hand instrument 10". For example, the sleeve-shaped chip chamber 30" can be attached or screwed onto the remaining hand instrument. With a medical hand instrument 10" of this type, an even narrower distal area can be realized in order to be able to scrape bone from otherwise inaccessible areas. The disadvantage in this case is the small capacity of the shaving chamber 30".

Now to the second variant of the medical hand instrument 10:

In the second variant of the medical hand instrument 10, the handpiece 20 also extends along a longitudinal axis 22 and is similarly shaped to the handpiece of the variant shown in FIG. 1 to. This can be seen in the perspective views in FIGS. 21, 22, 23 and 28 and the side views in FIGS. 26*a* to 26*d*. There is a difference to the variants and sub-variants of the medical hand instrument 10 shown previously in FIGS. 1 to 20 with regard to the type and arrangement of the scraping blade and the chip chamber.

In the second variant of the medical hand instrument 10, the scraping blade 60 is formed by a conical disk, the peripheral edge of which forms the cutting edge 62 and which has a diameter of between 4 mm and 6 mm, for example of 5 mm. In alternative embodiments, the scraping blade 60 may also have a larger diameter, for example 8 mm, 10 mm or 12 mm. The scraping blade 60 is connected to a shank 64, which is connected to the center of the scraping blade 60 on the inner side in the region of the tip 66 of the cone-shaped disk forming the scraping blade 60.

The chip chamber 30'" has the shape of a hollow cylinder, in the center of which the shaft 64 extends. The diameter of the shaft 64 is smaller than the inner diameter of the chip chamber 30', so that a hollow space is created between the outer surface of the shaft 64 and the inner wall of the chip chamber 30'", which is used to collect chips.

Figure 24:
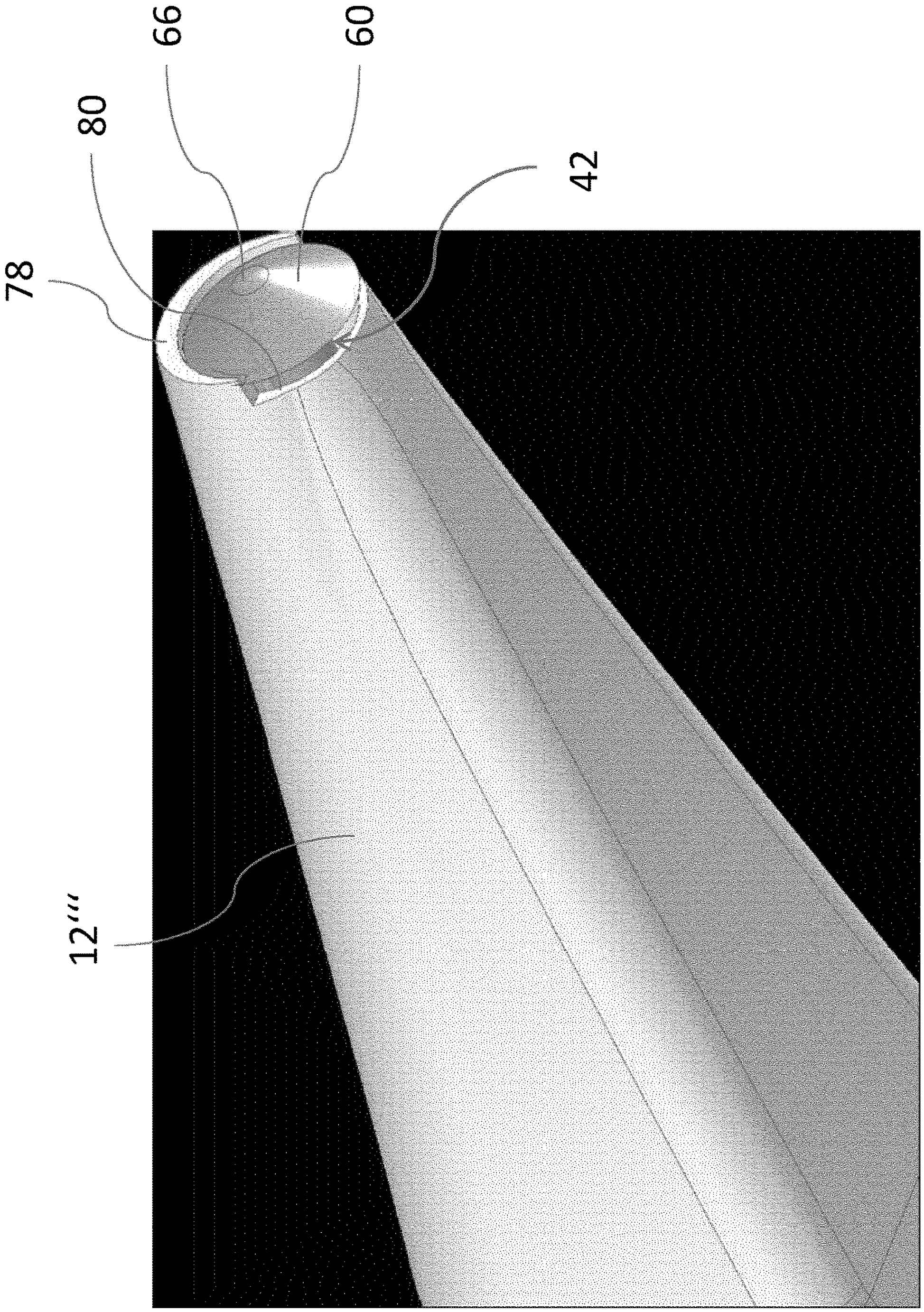
FIG. 24: a perspective detail view of the distal end of the second variant of the medical hand instrument.

The medical hand instrument 10 is shaped in the region of the distal end of the chip chamber 30'" such that a protrusion 78 at the distal end of the base body 12'" encloses the scraping blade 60 in a first circumferential portion of the scraping blade 60, while a second circumferential portion of the scraping blade 60 is exposed when the scraping blade 60 is in its working position; see FIG. 24. In the region of the second, free-standing circumferential portion of the scraping blade 60, the distal end of the base body 12 is shortened in such a way that a partial annular gap 42''' is formed, through which bone chips can pass into the chip chamber 30'''. The distal end of the base body 12''' of the medical hand instrument 10 thus has a stepped shape, with the distal forwardly projecting protrusion 78 of the base body 12''' enclosing the first circumferential portion of the scraping blade 60, while an end wall 80 of the base body 12''', which projects back in the longitudinal direction of the base body 12, defines the gap 42''', which leads to the chip chamber 30''', in the longitudinal direction. The gap 42''' is thus located between the cutting edge 62 of the scraping blade 60 and the end wall 80 of the base body 12''' of the hand instrument 10, which recedes in the axial direction.

During scraping, tensile forces act in the shaft 64 and are transmitted to the scraping blade 60. The material to be scraped exerts forces on the scraping blade 60 in the opposite direction to the tensile force, resulting in a torque. In order to absorb this torque and to support the scraping blade 60, a support and bearing surface 84 is provided at the distal end of the base body 12''', which lies in a plane extending perpendicularly to the longitudinal axis of the shaft 64, which is offset distally with respect to the plane in which the end face 80 extends by the width of the gap 42''' resulting therefrom. The support and contact surface 84 is bordered by the forwardly projecting protrusion 78 of the base body 12'''. The forwardly projecting protrusion 78 of the base body 12''' absorbs forces acting on the scraping blade transversely to the longitudinal axis of the shaft 64. Due to the shank 64, the and the forwardly projecting protrusion 78 of the base body 12''', the scraping blade is optimally stabilized in its working position for scraping and held in such a way that the forces acting during scraping are introduced into the base body 12''' without the shank 64 and scraping blade 60 being able to deform more strongly under the influence of the acting forces.

This means that forces introduced into the scraping blade 60 by a user via the ergonomically shaped handpiece 20 can be implemented in a very controlled manner for precise and effective scraping. The ergonomic shape of the handpiece 20 and the design of the scraping blade 60 and the distal end of the base body 12''' thus have a synergistic effect, which allows particularly precise and effective handling of the instrument 10.

Figure 25:
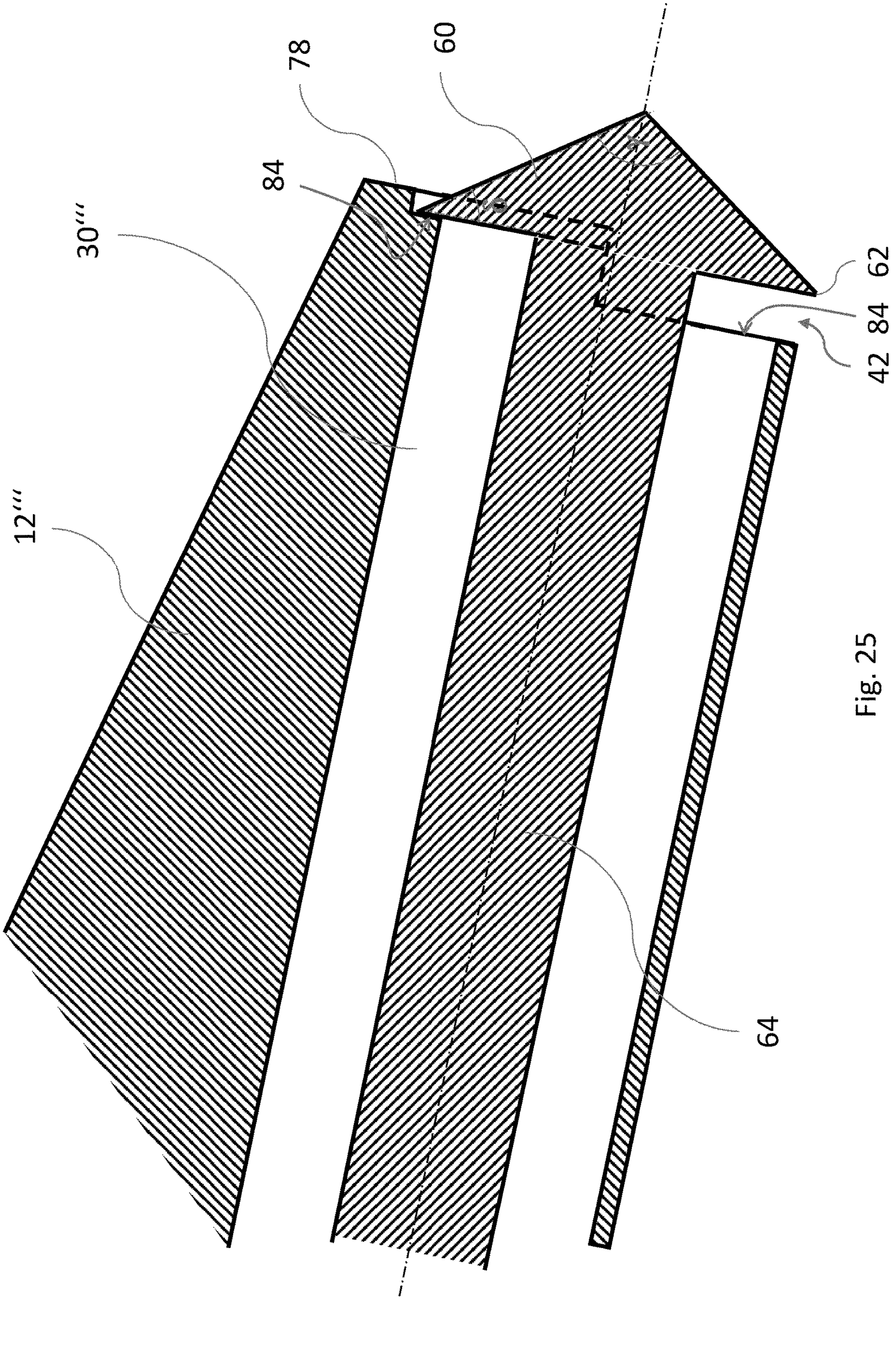
FIG. 25: a longitudinal section through the distal end of the second variant of the medical hand instrument.
Figure 26:
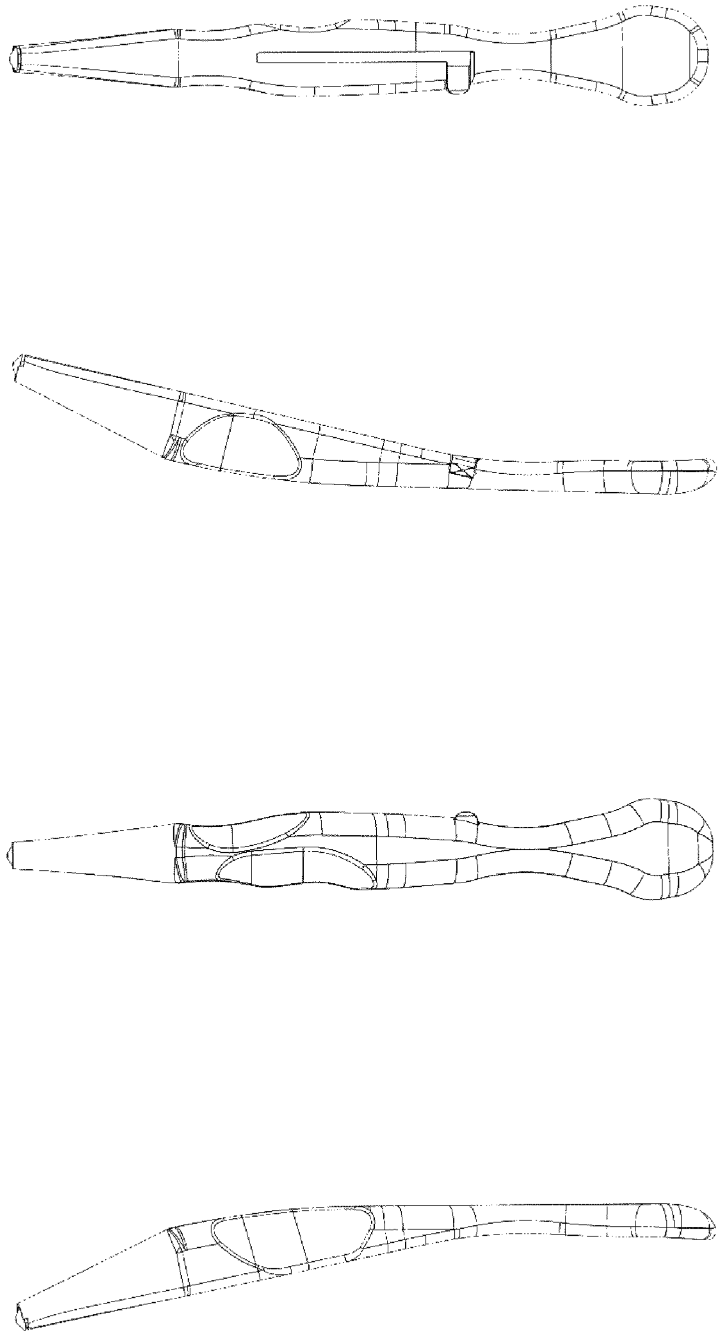
FIG. 26: views of the four long sides of the medical hand instrument a) from the left, b) from above, c) from the right and d) from below.
Figure 27:
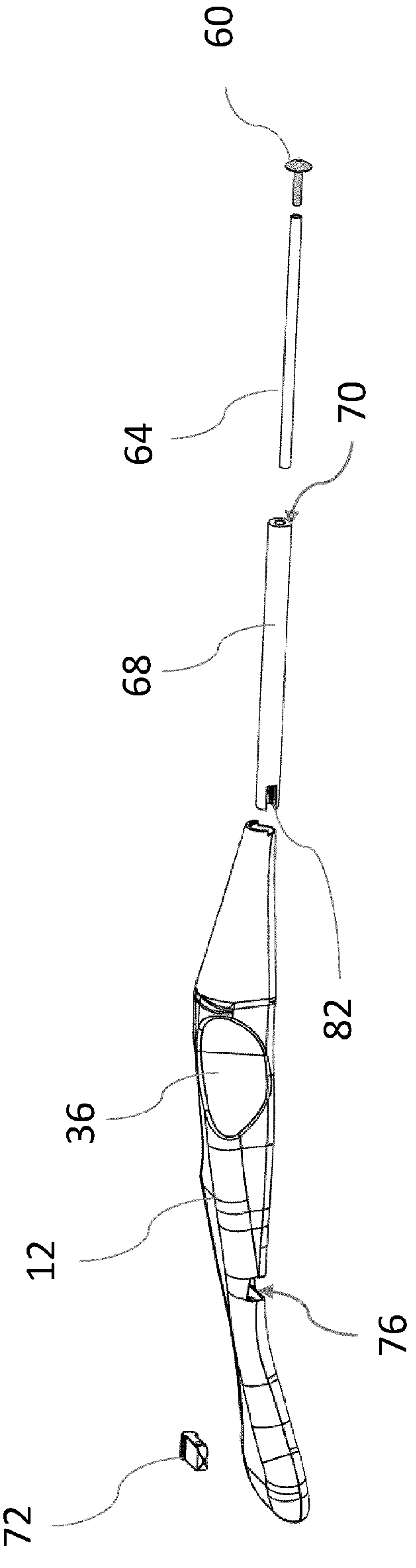
FIG. 27: a perspective exploded view of the medical hand instrument.
Figure 28:
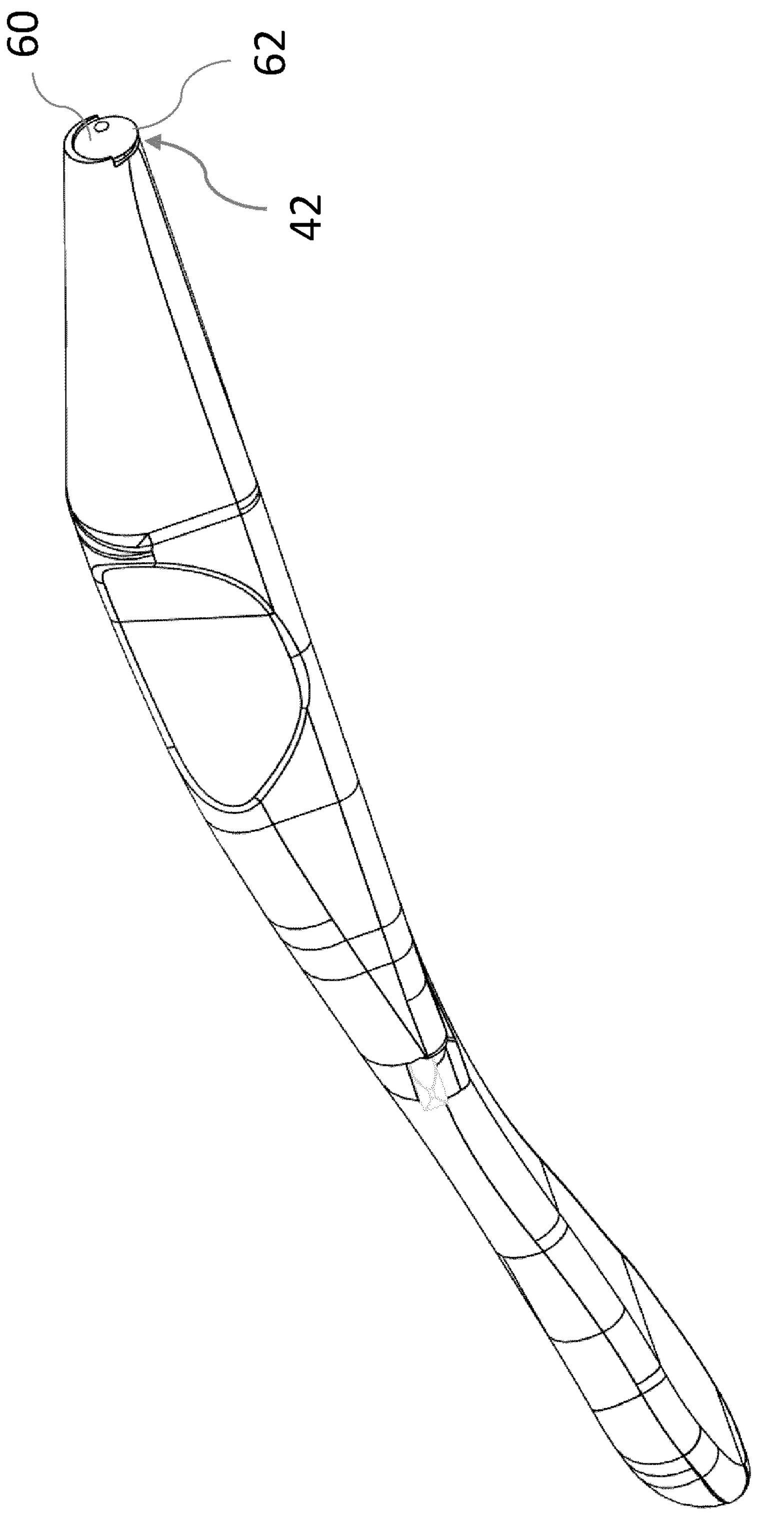
FIG. 28: a perspective view of the second variant of the medical hand instrument from the front.

The scraping blade 60 is designed as a conical disk and can have the shape of a blunt cone with a tip angle γ of approximately 110°, as shown in FIG. 25. In contrast to what is shown in FIG. 25, the tip 66 of the scraping blade 60 is preferably rounded. The tip angle of 110° leads to a cutting edge angle δ of the circumferential cutting edge 62 of 35°, provided that the scraping blade is not hollow, but has a flat rear side as shown.

The outer diameter of the ejector 68 corresponds approximately to an inner diameter of the chip chamber 30''', so that an end wall 70 of the ejector 68 delimits the chip chamber 30''' in its longitudinal direction when the scraping blade 60 is in the working position, but the ejector 68 can be displaced in the chip chamber 30'''.

Figure 29:
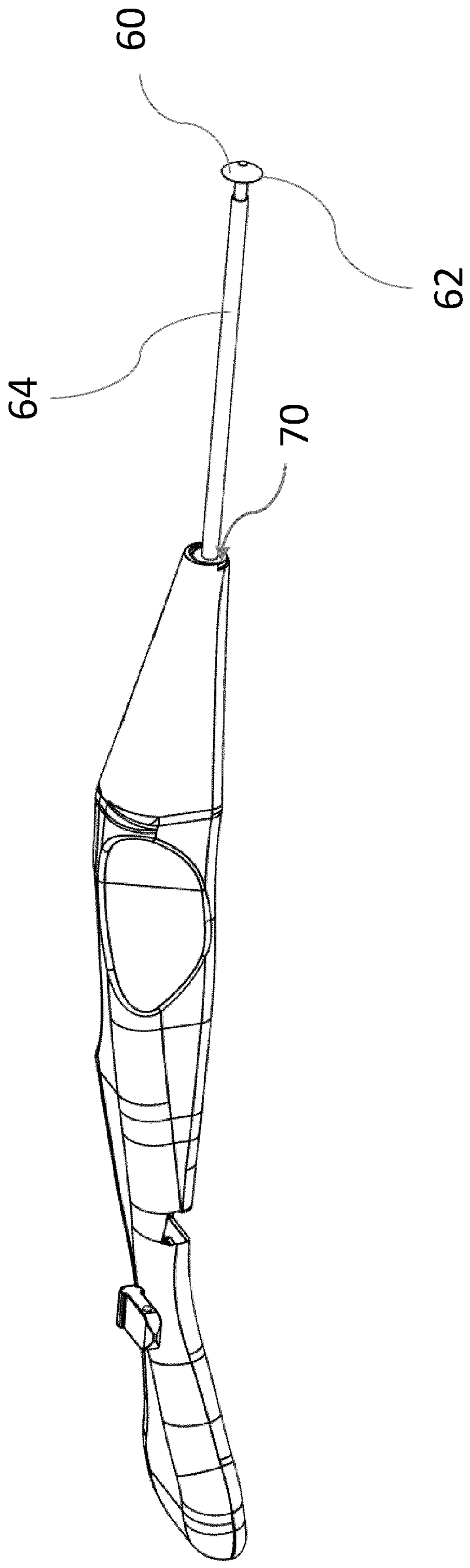
FIG. 29: a perspective overall view of the second variant of the medical hand instrument with scraping blade and shaft in the extended ejection position.

To eject bone chips, the ejector 68 together with the shaft 64 in the scraping blade 60 can be pushed axially forwards out of the main body 12''', as shown in FIG. 29. A handle 72 is provided for this purpose, which is attached to the proximal end of the ejector 68 and is guided in a longitudinal groove 74 in the base body 12''' of the hand instrument 10. With the aid of the handle 72, the scraping blade 60, the shaft 64 and the ejector 68 can be axially displaced from a working position into the ejection position and back. In doing so, the handle 72 moves in the longitudinal groove 74. The handle 72 can be an integral part of the ejector 68 or it can be attached to the ejector 68 as a separate part. For this purpose, the ejector 68 can have a recess 82 at its proximal end, into which a radially inwardly pointing end of the handle 72 can be inserted, see FIG. 27.

Figure 23:
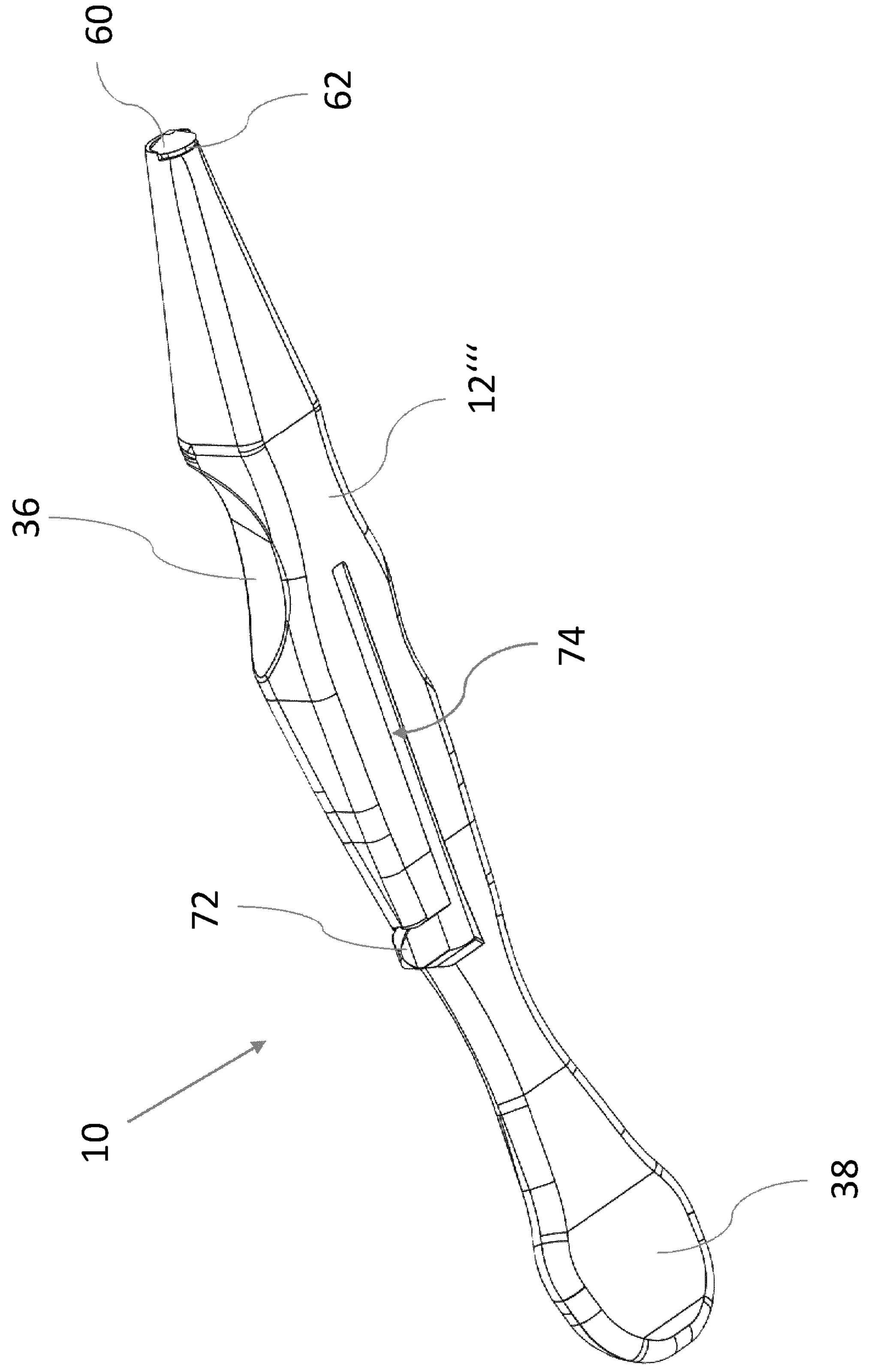
FIG. 23: a perspective view of the second variant of the medical hand instrument from below.

In order to fix the scraping blade 60 with the shank 64 in the ejector 68 in the working position of the scraping blade 60, the handle 72 can then be pivoted around the longitudinal axis of the shank 64 and the ejector 68 into a locking recess 76 when the scraping blade 60 is in the working position; see FIG. 23. When the handle 72 is pivoted into the recess 76, the handle 72 can no longer be moved back and forth along the longitudinal groove 74.

In order to use the medical hand instrument 10 for scraping according to the second variant, the scraping blade 60 together with the shaft 64 and the ejector 68 must be in the working position in which the scraping blade is partially enclosed by the distal end of the main body 12''' of the hand instrument 10. The handle 72 must be pivoted into the arresting recess 76 so that tensile forces can be transmitted from the base body 12''' of the hand instrument 10 via a distal wall of the arresting recess 76 to the handle 72 and from the latter via the ejector 68 and the shaft 64 to the scraping blade 60. This state is shown in FIGS. 21 to 25 and 27.

In order to be able to empty the chip chamber 30''' of the medical hand instrument 10 after use, the handle 72 must be pivoted out of the locking recess 76 and positioned in such a way that the handle 72 can be pushed forward in the longitudinal groove 74. This also moves the ejector 68, the shank 64 and the scraping blade 60 forwards, i.e. in a distal direction. In the process, the end wall 70 of the ejector 68 pushes material located in the chip chamber 30''' out of the chip chamber 30''' in a distal direction.

In the illustrated embodiment example, the ejector 68 is designed as an elongated cylindrical body, the outer diameter of which corresponds approximately to the inner diameter of the chip chamber 30''' and to which the shaft 64 is attached distally. This design of the ejector 68 has the advantage that the circumferential surface of the ejector 68 and the inner wall of the chip chamber 30''' provide secure longitudinal guidance. In the exploded view in FIG. 27, all components of this embodiment of the medical hand instrument are shown, including the elongated ejector 68 with its end surface 70.

Figure 30:
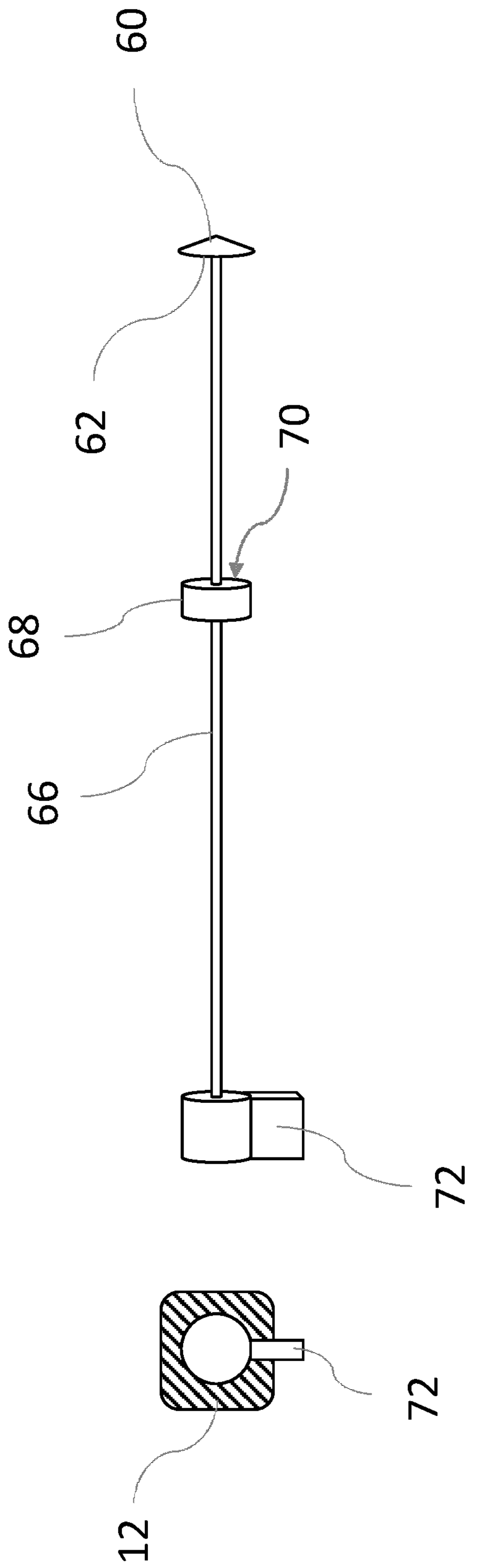
FIG. 30: an alternative design of the construction unit consisting of handle, shaft, ejector and scraping blade of the medical hand instrument.

In an alternative embodiment shown in FIG. 30, the ejector 68 may also be formed as a type of disk attached to the shaft 64. In this embodiment, the shaft 64 extends through the disk-shaped ejector 68 as far as the handle 72. In this case, sufficient longitudinal guidance can be ensured by the fact that the handle 72 is designed such that it is securely guided along the longitudinal groove 64 not only laterally, but in all radial directions. A corresponding design of the base body 12 and the handle 72 are shown in a cross-sectional sketch in FIG. 30*a*.

In a further embodiment, not shown, the shaft is continuous and angled at its proximal end so that the angled end of the shaft forms the handle for advancing and retracting the scraping blade and ejector. Because the shaft in this embodiment is continuous and in one piece from the scraping blade to its angled end forming the handle, it can transmit high tensile forces.

The scraping blade 60 is preferably made of stainless medical steel, for example 316L. The shaft 64 is also preferably made of stainless steel. The ejector 68 and the handle 72 are preferably made of plastic. In an embodiment, the ejector 68 and the handle 72 may be integrally formed, i.e., the handle 72 is formed as a lateral protrusion on the distal end of the ejector 68. In the other embodiment, in particular the embodiment in which the ejector is in the form of a disk or short cylinder attached to the shaft 64, the ejector 68 and the handle 72 are separately connected to the shaft 64.

REFERENCE SIGN

10 Hand instrument
12 Base body
14 distal end
16 proximal end
18 Scraping blade
20 Handpiece
22 Longitudinal axis
24 Blade plane
26 Cutting edge
28 Cutting angle
30 Chip chamber
32 Finger rest for middle finger
34 Finger rest for thumb or index finger
36 Finger rest for thumb or index finger
38 Support rest
40 Chip chamber lid
42 Gap
44 Screw
46 Thread
48 Countersunk head
50 Deepening
52 Fastening opening
54 Ring blade
56 central opening in the ring blade
60 disc scraping blade (conical disc)
62 Cutting edge of the scraping blade
64 Shank to the distal end of which the scraping blade is attached
66 Tip of the conical disk forming the scraping blade
68 Ejector for ejecting chips from the chip chamber
70 End wall of the ejector
72 Handle for pushing the shaft, ejector and scraping blade forwards and backwards
74 Longitudinal groove for the handle
76 Recess for locking the handle
78 Protrusion at the distal end of the main body
80 End wall of the main body
82 Recess at the proximal end of the ejector for attaching the handle
84 Support and contact surface for the scraping blade
$\alpha$ cutting angle
$\beta$ guide angle
$\gamma$ tip angle
$\delta$ cutting edge angle

What is claimed is:

1. A hand instrument having a handpiece and a scraping blade arranged distally of the handpiece and a chip chamber, of which the scraping blade is designed for scraping in particular bones and is arranged in such a way that chips scraped by means of the scraping blade enter the chip chamber and the scraping blade extends in a plane inclined with respect to a longitudinal axis of the handpiece, wherein the handpiece is designed as a handle with three finger rests and a proximal support rest, the three finger rests being inclined to one another in such a way that the three finger rests extend at an angle of less than 90° to one another in a cross-section through the handpiece and whereby a first finger rest is positioned on a same side of the hand instrument as the scraping blade and a second finger rest and a third finger rest are inclined towards to the first finger rest, whereby in a cross section of the handpiece the second finger rest and first finger rest form an angle of less than 90° between them and the third finger rest and the first finger rest form an angle of less than 90° between them.

2. The hand instrument according to claim 1, wherein the three finger rests are designed as depressions having a concave shape in the longitudinal direction of the handpiece.

3. The hand instrument according to claim 1, wherein the support rest is formed by a concave surface at the proximal end of the handpiece, which is oriented in a radial direction of the handpiece in which an outer flat side of the scraping blade is oriented.

4. The hand instrument according to claim 3, wherein the support rest extends in the longitudinal direction of the hand instrument at an obtuse angle of between 0° and 10° with respect to the outer flat side of the scraping blade.

5. The hand instrument according to claim 1, wherein the width of the handpiece in a region of the finger rests is between 11 mm and 16 mm.

6. The hand instrument according to claim 1, wherein the width of the handpiece in a region of the support rest is between 20 mm and 25 mm and initially decreases in the distal direction and increases again in a region of the finger rests.

7. The hand instrument according to claim 1, wherein the chip chamber has a volume of more than 3.5 $cm^3$, preferably more than 4 $cm^3$.

8. The hand instrument according to claim 1, wherein the scraping blade extends substantially, in particular with the exception of a cutting edge, in a blade plane which is inclined by at least 50° with respect to the longitudinal axis (22) of the handpiece.

9. The hand instrument according to claim 1, wherein the handpiece is made of thermoplastic material, preferably of polycarbonate Makrolon 2458 or polyamide ixef 1022 approved for medical use.

10. The hand instrument according to claim 1, wherein the chip chamber and the handpiece are formed in one piece and are part of a one-piece base body to which the scraping blade and a chip chamber closure in the form of a removable cover are attached.

11. The hand instrument according to claim 1, wherein the scraping blade is designed as a conical disc and is attached to a shaft which is arranged in the handpiece so as to be longitudinally displaceable.

12. The hand instrument according to claim 11, wherein the chip chamber is formed as a cylindrical cavity concentrically surrounding the shaft, which is open at the distal end of the handpiece.

13. The hand instrument according to claim 11, comprising an ejector, which is longitudinally displaceable together with the scraping blade and the shaft and has an axial distance from the scraping blade, the chip chamber extending in the axial direction between the scraping blade and an end wall of the ejector.

14. The hand instrument according to claim 11, wherein the shaft can be locked with the scraping blade in such a way that the shaft and the scraping blade can no longer be longitudinally displaced with respect to the handpiece in the locked state and the scraping blade is locked in a working position serving for scraping in such a way that tensile forces can be introduced into the shaft by means of the handpiece and transmitted to the scraping blade.

15. The hand instrument according to claim 11, wherein the shaft is at least indirectly connected to a handle which serves for longitudinally displacing the shaft and the scraping blade with respect to the handpiece.

16. The hand instrument according to claim 15, wherein the handpiece has a longitudinal groove for guiding the handle.

17. The hand instrument according to claim 16, wherein the handle of the handpiece has a recess at the proximal end of the longitudinal groove into which the handle can be pivoted by means of a rotary movement around the longitudinal axis of the shaft in order to lock the shaft and the scraping blade in a working position.

18. The hand instrument according to claim 1, wherein a third finger rest for a middle finger of a user is located on a same side of the handpiece as the scaping blade and wherein the first finger rest and the second finger rest are located on another side of the handpiece for respective use by an index of the user and by a thumb of the user.

* * * * *